United States Patent [19]

Takaya et al.

[11] Patent Number: 4,493,831

[45] Date of Patent: Jan. 15, 1985

[54] AMINOGLYCOSIDE DERIVATIVES

[75] Inventors: Takao Takaya, Kawanishi; Nobuyoshi Yasuda, Nishinomiya; Hideo Tsutsumi, Toyonaka; Keiji Matsuda, Takatsuki, all of Japan

[73] Assignee: Fujisawa Pharmaceutical Co., Ltd., Osaka, Japan

[21] Appl. No.: 537,967

[22] Filed: Sep. 30, 1983

[30] Foreign Application Priority Data

Oct. 25, 1982 [GB] United Kingdom ............ 8230421
Apr. 18, 1983 [GB] United Kingdom ............ 8310436

[51] Int. Cl.$^3$ .................. A61K 31/71; C07H 15/22
[52] U.S. Cl. ................................ 424/180; 536/13.7; 536/13.8
[58] Field of Search .................... 536/13.7, 13.8; 424/180

[56] References Cited

U.S. PATENT DOCUMENTS 4,160,082  7/1979  Million et al. ............ 536/13.8
4,178,437  12/1979  Thomas ..................... 536/13.8

*Primary Examiner*—Johnnie R. Brown
*Assistant Examiner*—Elli Peselev
*Attorney, Agent, or Firm*—Oblon, Fisher, Spivak, McClelland & Maier

[57] ABSTRACT

Aminoglycoside derivatives and pharmaceutically acceptable salts thereof which are useful as prophylactic and therapeutic agents for infectious diseases caused by pathogenic microorganisms, processes for the preparation thereof and a pharmaceutical composition comprising the same.

18 Claims, No Drawings

AMINOGLYCOSIDE DERIVATIVES

BACKGROUND OF THE INVENTION

Field of the Invention

This invention relates to new aminoglycoside derivatives and pharmaceutically acceptable salts thereof. More particularly, it relates to new aminoglycoside derivatives and pharmaceutically acceptable salts thereof which have antiviral activity, and immunostimulating activity, processes for the preparation thereof and a pharmaceutical composition comprising the same.

DESCRIPTION OF THE PREFERRED EMBODIMENTS

This invention provides new aminoglycoside derivatives which are useful as prophylactic and therapeutic agents for infectious diseases caused by pathogenic microorganisms.

This invention provides processes for preparing the aminoglycoside derivatives.

This invention provides a pharmaceutical composition comprising the aminoglycoside derivatives.

The new aminoglycoside derivatives of this invention can be represented by the following formula:

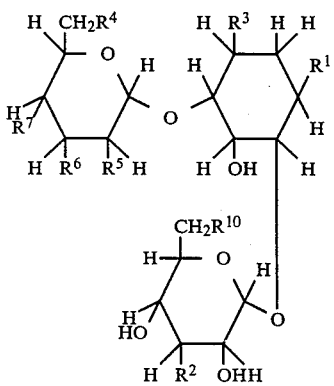

(I)

wherein at least one $R^1$, $R^2$, $R^3$ and $R^4$ is higher alkanoylamino, higher alkenoylamino, higher alkoxycarbonylamino, higher alkylaminocarbonylamino, higher alkoxy(lower)alkanoylamino or higher alkylthiocarbonylamino, each of which may have suitable substituent(s), and the others are amino or acylamino,
$R^5$ is hydroxy, amino or acylamino,
$R^6$ and $R^7$ are each hydroxy or hydrogen, and
$R^{10}$ is hydroxy or phosphonoxy.

According to this invention, the new aminoglycoside derivatives (I) can be prepared by, for example, the following processes.

Process 1:

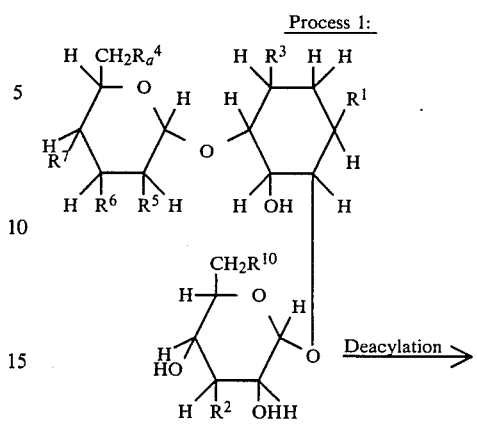

(Ia)
or a salt thereof

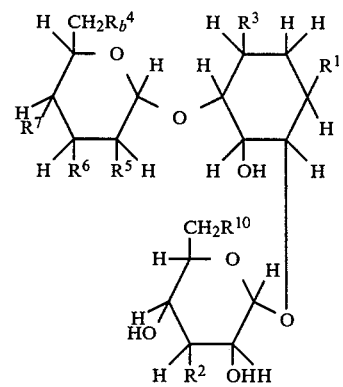

(Ib)
or a salt thereof wherein $R^5$, $R^6$, $R^7$ and $R^{10}$ are each as defined above,
$R_a^4$ is acylamino,
$R_b^4$ is amino, and
at least one of $R^1$, $R^2$ and $R^3$ is higher alkanoylamino, higher alkenoylamino, higher alkoxycarbonylamino, higher alkylaminocarbonylamino, higher alkoxy(lower)alkanoylamino or higher alkylthiocarbonylamino, each of which may have suitable substituent(s), and the others are amino or acylamino.

Process 2:

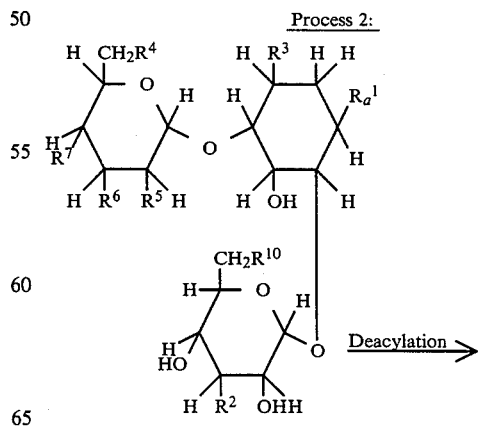

(Ic)
or a salt thereof

Process 2:

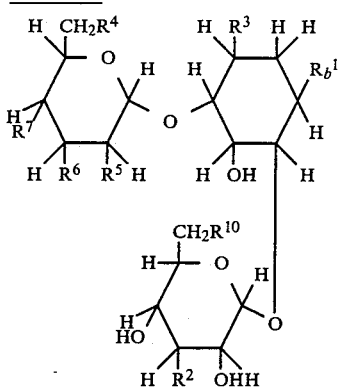

(Id)
or a salt thereof wherein $R^5$, $R^6$, $R^7$ and $R^{10}$ are each as defined above,
$R_a^1$ is acylamino,
$R_b^1$ is amino, and
at least one of $R^2$, $R^3$ and $R^4$ is higher alkanoylamino, higher alkenoylamino, higher alkoxycarbonylamino, higher alkylaminocarbonylamino, higher alkoxy(-lower)alkanoylamino or higher alkylthiocarbonylamino, each of which may have suitable substituent(s), and the others are amino or acylamino.

Process 3:

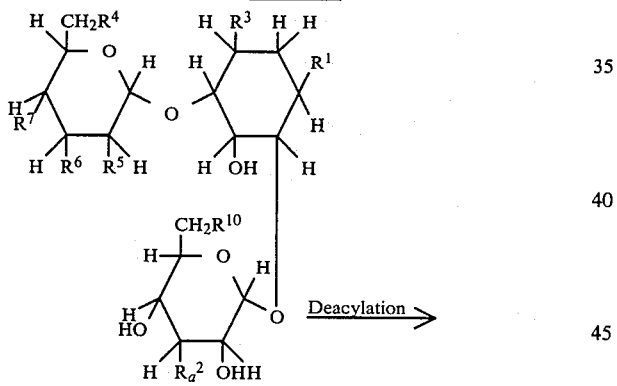

Deacylation →

(Ie)
or a salt thereof

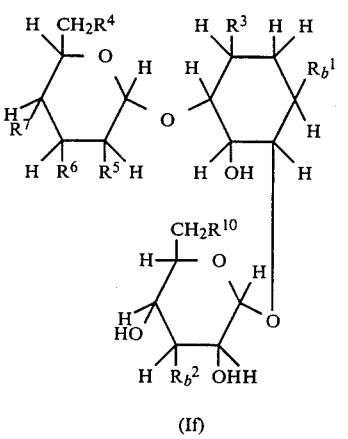

(If)
or a salt thereof wherein $R^5$, $R^6$, $R^7$ and $R^{10}$ are each as defined above,
$R_a^2$ is acylamino,
$R_b^2$ is amino, and
at least one $R^1$, $R^3$ and $R^4$ is higher alkanoylamino, higher alkenoylamino, higher alkoxycarbonylamino, higher alkylaminocarbonylamino, higher alkoxy(-lower)alkanoylamino or higher alkylthiocarbonylamino, each of which may have suitable substituent(s), and the others are amino or acylamino.

Process 4:

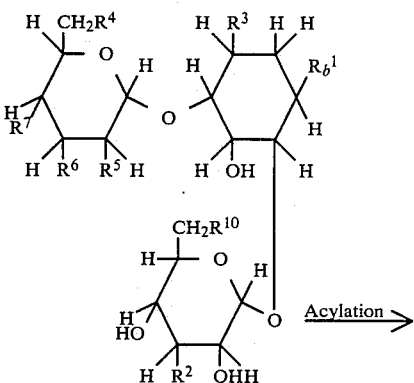

Acylation →

(IIb)
or its reactive derivative at the amino group or a salt thereof

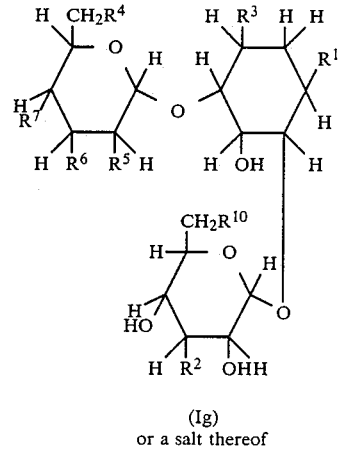

(Ig)
or a salt thereof wherein $R_b^1$, $R^5$, $R^6$, $R^7$ and $R^{10}$ are each as defined above,
$R^1$ is higher alkanoylamino, higher alkenoylamino, higher alkoxycarbonylamino, higher alkylaminocarbonylamino, higher alkoxy(lower)alkanoylamino or higher alkylthiocarbonylamino, each of which may have suitable substituent(s), and
$R^2$, $R^3$ and $R^4$ are each amino or acylamino.

Process 5:

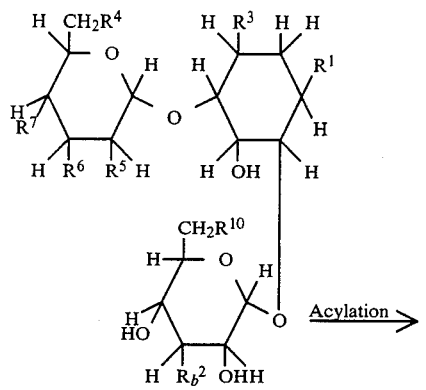

(IId)
or its reactive derivative
at the amino group
or a salt thereof

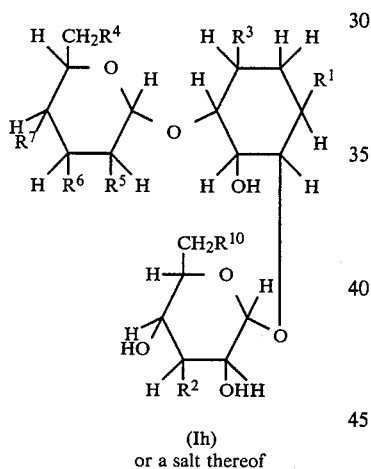

(Ih)
or a salt thereof wherein $R_b^2$, $R^5$, $R^6$, $R^7$ and $R^{10}$ are each as defined above, $R^2$ is higher alkanoylamino, higher alkenoylamino, higher alkoxycarbonylamino, higher alkylaminocarbonylamino, higher alkoxy(lower)alkanoylamino or higher alkylthiocarbonylamino, each of which may have suitable substituent(s) and $R^1$, $R^3$ and $R^4$ are each amino or acylamino.

Process 6:

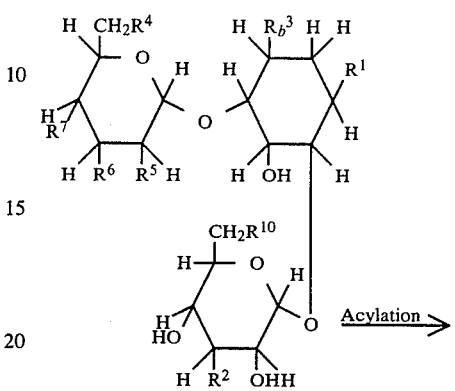

(IIf)
or its reactive derivative
at the amino group
or a salt thereof

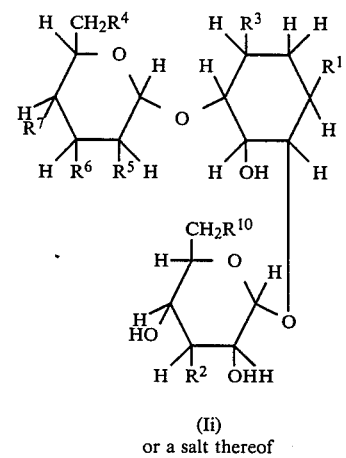

(Ii)
or a salt thereof wherein $R^5$, $R^6$, $R^7$ and $R^{10}$ are each as defined above, $R_b^3$ is amino, $R^3$ is higher alkanoylamino, higher alkenoylamino, higher alkoxycarbonylamino, higher alkylaminocarbonylamino, higher alkoxy(lower)alkanoylamino or higher alkylthiocarbonylamino, each of which may have suitable substituent(s), and $R^1$, $R^2$ and $R^4$ are each amino or acylamino.

Process 7:

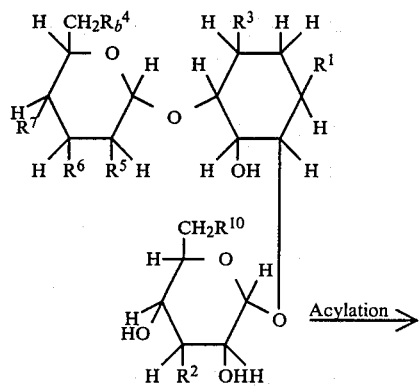

(IIh)
or its reactive derivative
at the amino group
or a salt thereof

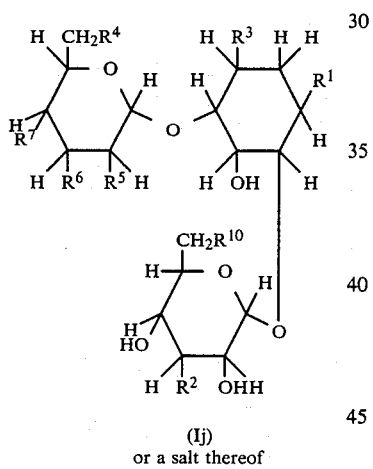

(Ij)
or a salt thereof

Process 8:

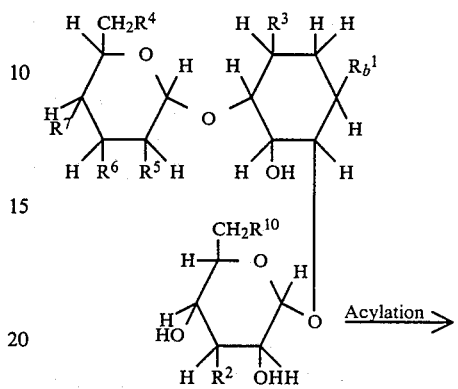

(Ik)
or its reactive derivative
at the amino group
or a salt thereof

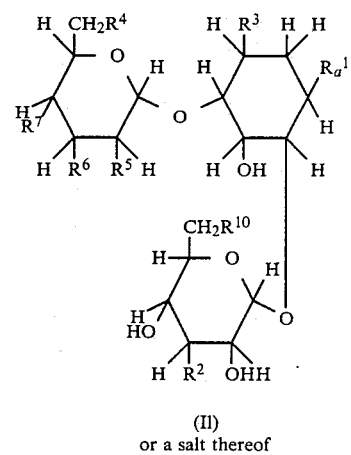

(Il)
or a salt thereof wherein $R_b^4$, $R^5$, $R^6$, $R^7$ and $R^{10}$ are each as defined above, $R^4$ is higher alkanoylamino, higher alkenoylamino, higher alkoxycarbonylamino, higher alkylaminocarbonylamino, higher alkoxy(lower)alkanoylamino or higher alkylthiocarbonylamino, each of which may have suitable substituent(s), and $R^1$, $R^2$ and $R^3$ are each amino or acylamino.

wherein $R_a^1$, $R_b^1$, $R^5$, $R^6$, $R^7$ and $R^{10}$ are each as defined above, and at least one of $R^2$, $R^3$ and $R^4$ is higher alkanoylamino, higher alkenoylamino, higher alkoxycarbonylamino, higher alkylaminocarbonylamino, higher alkoxy(lower)alkanoylamino or higher alkylthiocarbonylamino, each of which may have suitable substituent(s), and the others are amino or acylamino.

Process 9:

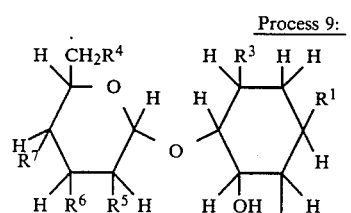

(Im)
or its reactive derivative
at the amino group
or a salt thereof

Acylation →

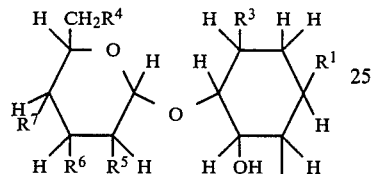

(In)
or a salt thereof wherein $R_a^2$, $R_b^2$, $R^5$, $R^6$, $R^7$ and $R^{10}$ are each as defined above, and at least one $R^1$, $R^3$ and $R^4$ is higher alkanoylamino, higher alkenoylamino, higher alkoxycarbonylamino, higher alkylaminocarbonylamino, higher alkoxy(lower)alkanoylamino or higher alkylthiocarbonylamino, each of which may have suitable substituent(s), and the others are amino or acylamino.

Process 10:

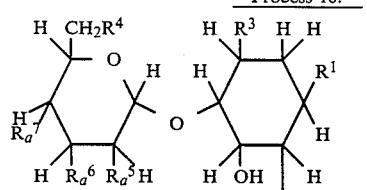

(IIm')
or a salt thereof

Deacylation →

-continued
Process 10:

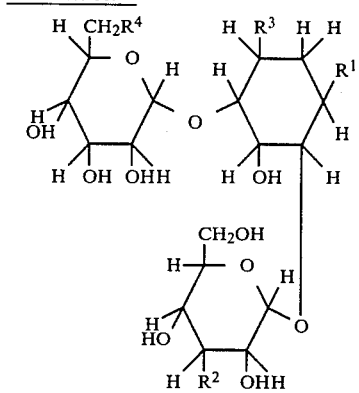

(Io)
or a salt thereof wherein $R_a^5$, $R_a^6$, $R_a^7$, $R_a^8$, $R_a^9$ and $R_a^{10}$ are each acyloxy, and at least one of $R^1$, $R^2$, $R^3$ and $R^4$ is higher alkanoylamino, higher alkenoylamino, higher alkoxycarbonylamino, higher alkylaminocarbonylamino, higher alkoxy(lower)alkanoylamino or higher alkylthiocarbonylamino, each of which may have suitable substituent(s), and the others are amino or acylamino.

Process 11:

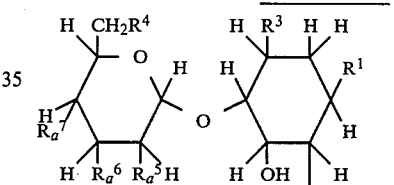

(IIq)
or a salt thereof

Elimination of phosohono protective group →

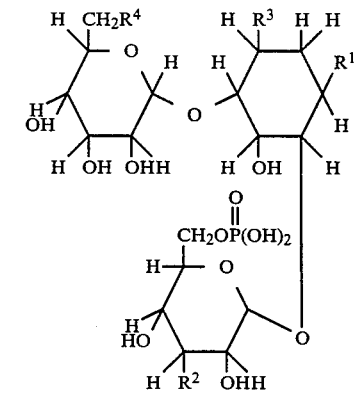

(Ip)
or a salt thereof wherein $R_a{}^5$, $R_a{}^6$, $R_a{}^7$, $R_a{}^8$, $R_a{}^9$ are each as defined above, $R_c{}^{10}$ is protected phosphonoxy, and at least one of $R^1$, $R^2$, $R^3$ and $R^4$ is higher alkanoylamino, higher alkenoylamino, higher alkoxycarbonylamino, higher alkylaminocarbonylamino, higher alkoxy(lower)alkanoylamino or higher alkylthiocarbonylamino, each of which may have suitable substituent(s) and the others are amino or acylamino.

Among the starting compounds in this invention, the compounds (IIb), (IId), (IIf), (IIh) and (IIm') and (IIq) are novel and can be prepared by the following processes.

Process A:

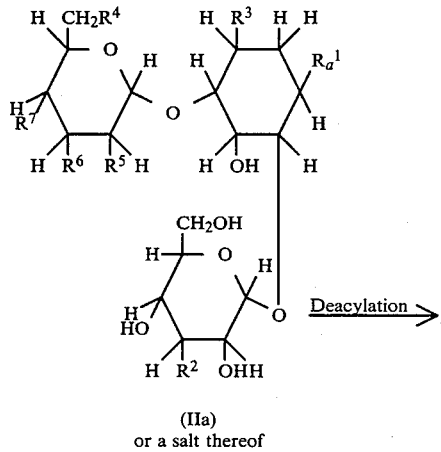

(IIa)
or a salt thereof

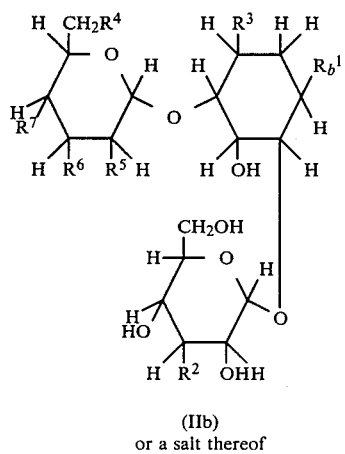

(IIb)
or a salt thereof wherein $R_a{}^1$, $R_b{}^1$, $R^5$, $R^6$ and $R^7$ are each as defined above, and $R^2$, $R^3$ and $R^4$ are each amino or acylamino.

Process B:

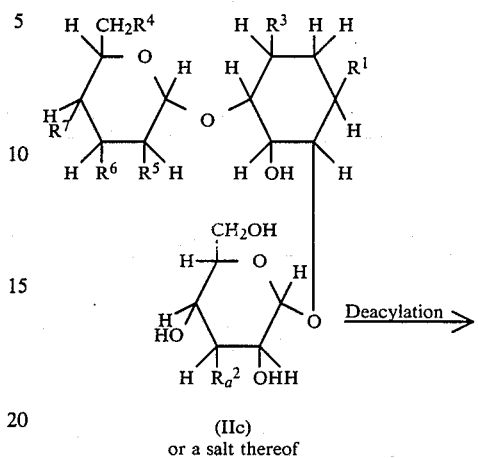

(IIc)
or a salt thereof

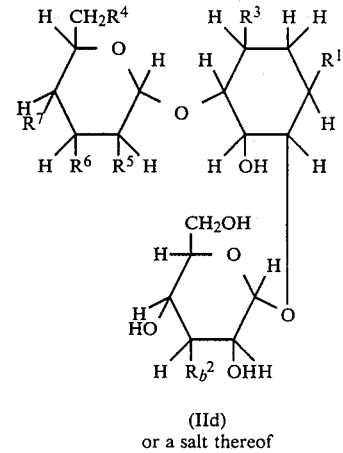

(IId)
or a salt thereof wherein $R_a{}^2$, $R_b{}^2$, $R^5$, $R^6$ and $R^7$ are each as defined above, and $R^1$, $R^3$ and $R^4$ are each amino or acylamino.

Process C:

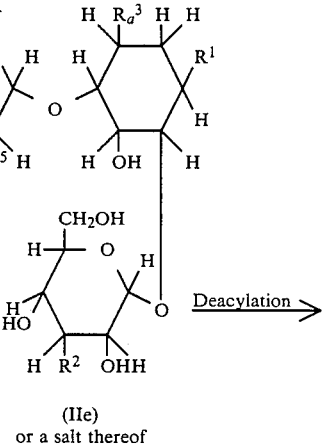

(IIe)
or a salt thereof

-continued

Process C:

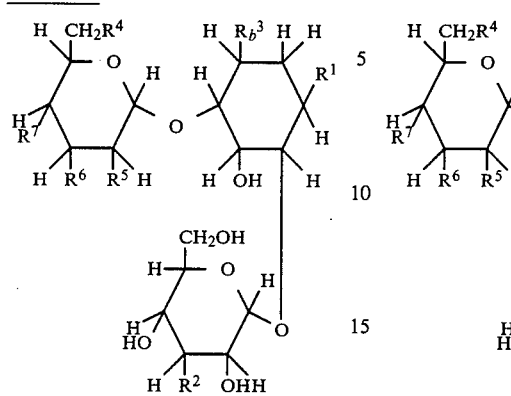

(IIf)
or a salt thereof wherein $R_b^3$, $R^5$, and $R^6$ and $R^7$ are each as defined above,
$R_a^3$ is acylamino, and
$R^1$, $R^2$ and $R^4$ are each amino or acylamino.

Process D:

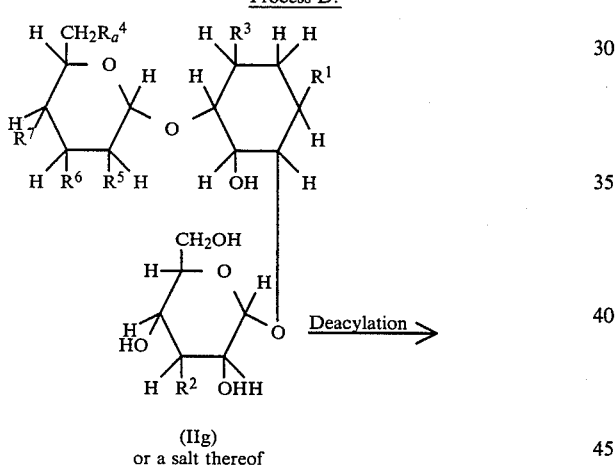

(IIg)
or a salt thereof wherein $R_a^4$, $R_b^4$, $R^5$, $R^6$ and $R^7$ are each as defined above, and
$R^1$, $R^2$ and $R^3$ are each amino or acylamino.

Process E:

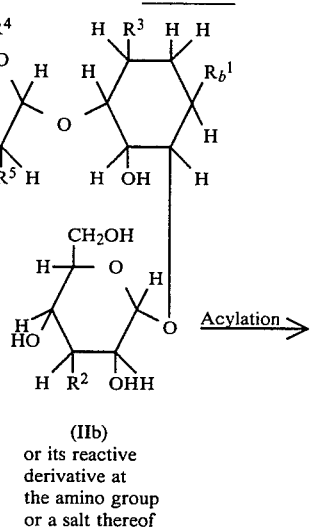

(IIb)
or its reactive
derivative at
the amino group
or a salt thereof

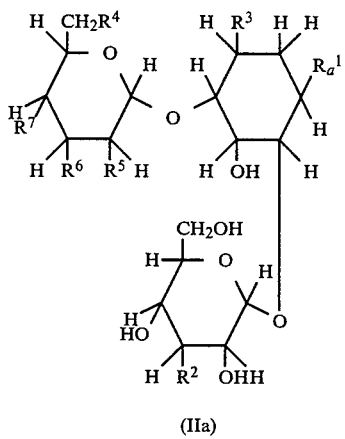

(IIa)
or a salt thereof wherein $R_a^1$, $R_b^1$, $R^5$, $R^6$ and $R^7$ are each as defined above, and
$R^2$, $R^3$ and $R^4$ are each amino or acylamino.

Process F:

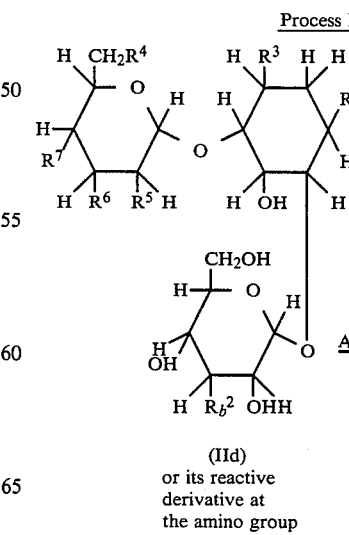

(IId)
or its reactive
derivative at
the amino group
or a salt thereof

Process F:

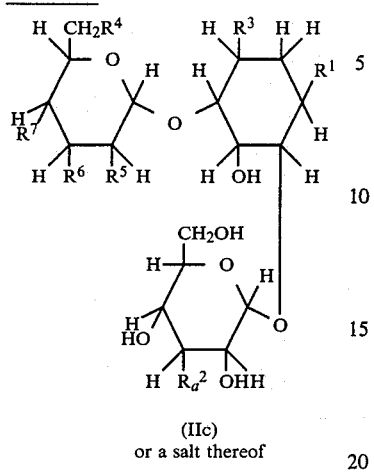

(IIc)
or a salt thereof wherein $R_a^2$, $R_b^2$, $R^5$, $R^6$ and $R^7$ are each as defined above, and
$R^1$, $R^3$ and $R^4$ are each amino or acylamino.

Process G:

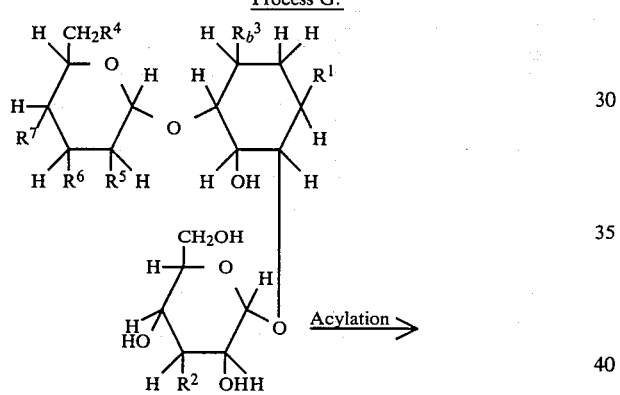

(IIf)
or its reactive derivative at the amino group or a salt thereof (IIe)
or a salt thereof wherein $R_a^3$, $R_b^3$, $R^5$, $R^6$ and $R^7$ are each as defined above, and
$R^1$, $R^2$ and $R^4$ are each amino or acylamino.

Process H:

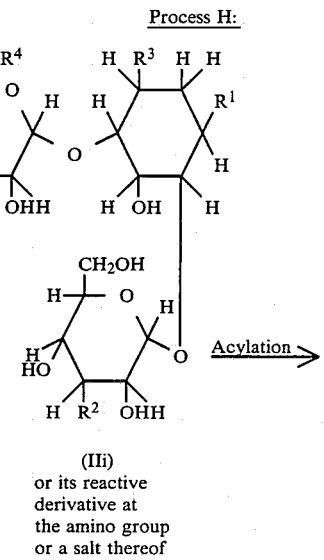

(IIi)
or its reactive derivative at the amino group or a salt thereof

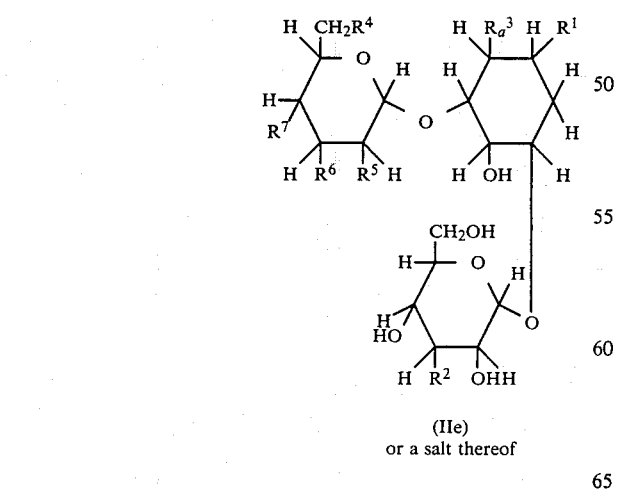

(IIj)
or a salt thereof wherein $R_a^5$, $R_a^6$, $R_a^7$, $R_a^8$, $R_a^9$ and $R_a^{10}$ are each as defined above, and
$R^1$, $R^2$, $R^3$ and $R^4$ are each amino or acylamino.

Process I:

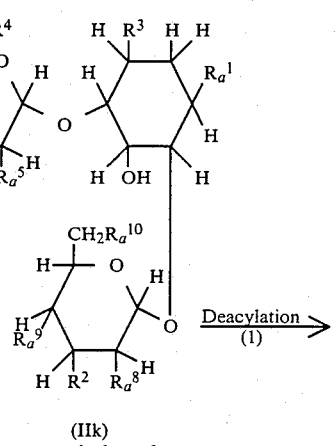

(IIk)
or a salt thereof

-continued
Process I:

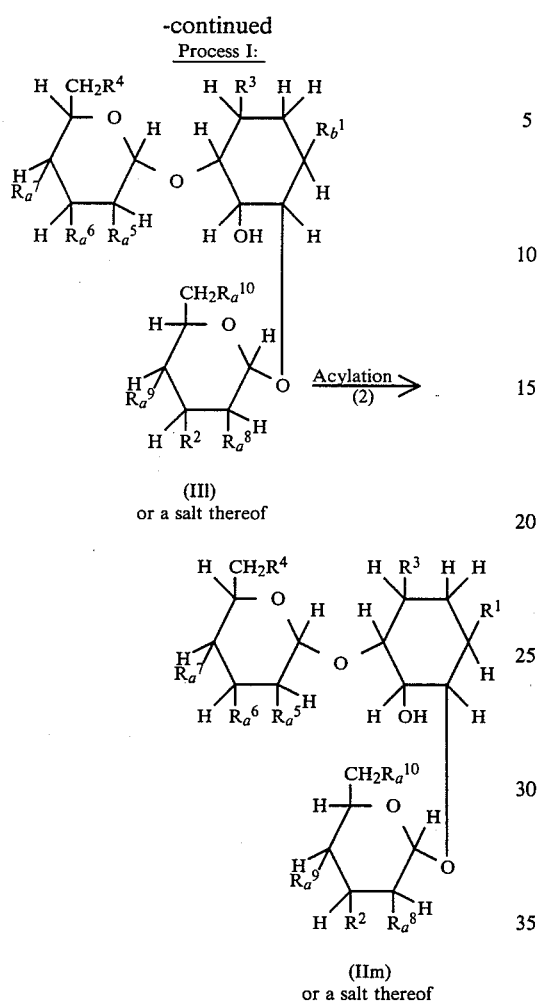

(III)
or a salt thereof (IIm)
or a salt thereof wherein $R_a{}^1$, $R_b{}^1$, $R_a{}^5$, $R_a{}^6$, $R_a{}^7$, $R_a{}^8$, $R_a{}^9$ and $R_a{}^{10}$ are each as defined above, and $R^1$ is higher alkanoylamino, higher alkenoylamino, higher alkoxycarbonylamino, higher alkylaminocarbonylamino, higher alkoxy(lower)alkanoylamino or higher alkylthiocarbonylamino, each of which may have suitable substituent(s), and $R^2$, $R^3$ and $R^4$ are each amino or acylamino.

Process J:

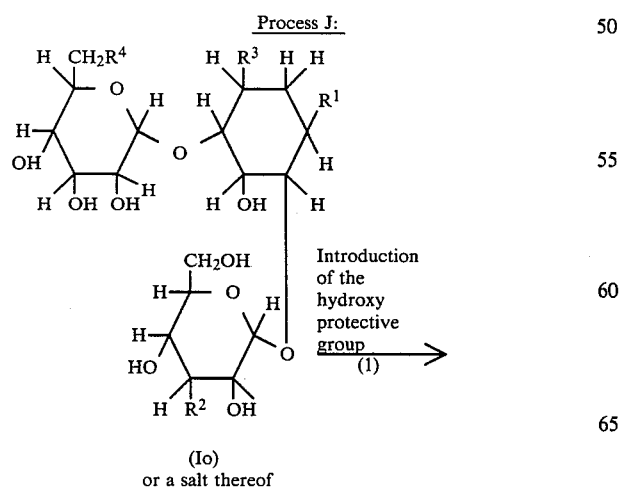

(Io)
or a salt thereof

Process J:

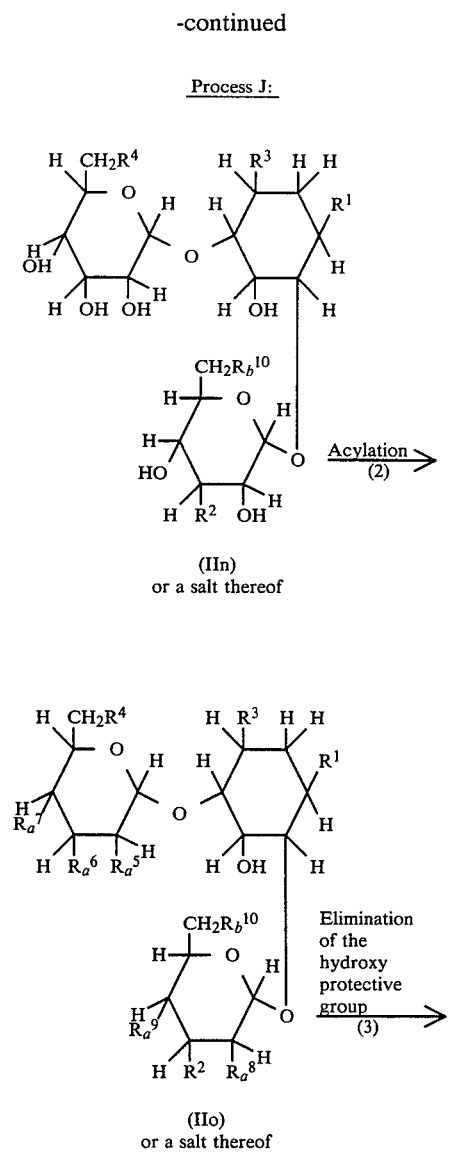

(IIn)
or a salt thereof (IIo)
or a salt thereof

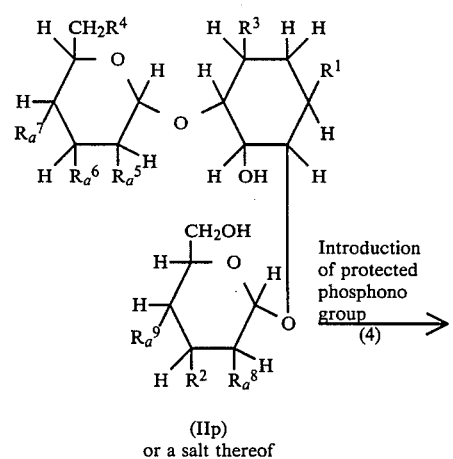

(IIp)
or a salt thereof

-continued
Process J:

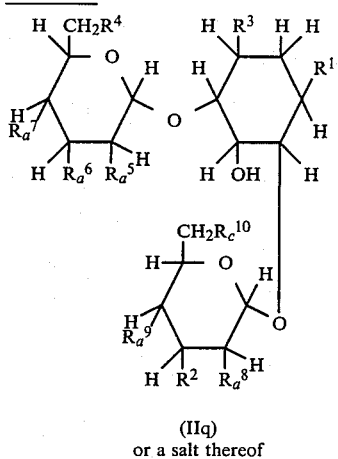

(IIq)
or a salt thereof wherein $R_a^5$, $R_a^6$, $R_a^7$, $R_a^8$ and $R_a^9$ are each as defined above,
$R_b^{10}$ is ar(lower)alkoxy,
$R_c^{10}$ is protected phosphonoxy, and
at least one of $R^1$, $R^2$, $R^3$ and $R^4$ is higher alkanoylamino, higher alkenoylamino, higher alkoxycarbonylamino, higher alkylaminocarbonylamino, higher alkoxy(lower)alkanoylamino or higher alkylthiocarbonylamino, each of which may have suitable substituent(s), and the others are amino or acylamino.

Suitable pharmaceutically acceptable salts of aminoglycoside derivatives (I) are conventional salts and may include an organic or an inorganic acid addition salt such as hydrochloride, hydrobromide, hydriodide, sulfate, nitrate, carbonate, phosphate, acetate, fumarate, maleate, tartrate, methanesulfonate, benzenesulfonate, toluenesulfonate and the like.

In the above and subsequent descriptions of this specification, suitable examples and illustrations of the various definitions are explained in detail in the following.

The term "lower" is intended to mean 1 to 6 carbon atom(s), unless otherwise provided.

Suitable "acyl" moiety in the terms "acylamino" and "acyloxy" may include carbamoyl, an aliphatic acyl, an aromatic acyl, a heterocyclic acyl and an aliphatic acyl substituted with aromatic or heterocyclic group(s).

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, butoxycarbonyl, tert-butoxycarbonyl, etc.), lower alkenoyl (e.g. acryloyl, methacryloyl, crotonoyl, etc.), ($C_3$–$C_7$)-cycloalkanecarbonyl (e.g. cyclohexanecarbonyl, etc.), and the like.

The aromatic acyl may include aroyl (e.g. benzoyl, toluoyl, xyloyl, etc.), arenesulfonyl (e.g. benzenesulfonyl, tosyl, etc.), and the like.

The heterocyclic acyl may include heterocyclic carbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include phenyl(lower)alkanoyl (e.g. phenylacetyl, phenylpropionyl, phenylhexanoyl, etc.), phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl, thiadiazolylpropionyl, and the like.

These acyl groups may be further substituted with suitable substituent(s) such as hydroxy, amino, carboxy, lower alkyl (e.g. methyl, ethyl, propyl, isopropyl, butyl, pentyl, hexyl, etc.), halogen (e.g. chloride, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro, acylamino, aryloxy (e.g., benzyloxy, tolyloxy, etc.), lower alkanoyloxy (e.g. formyloxy, acetyloxy, propionyloxy, butyryloxy, isobutyryloxy, valeryloxy, isovaleryloxy, pivaloyloxy, hexanoyloxy, etc.), and the like, and the preferable acyl having such substituent(s) may be mono (or di or tri) halo(lower)alkanoyl (e.g., chloroacetyl, bromoacetyl, dichloroacetyl, trifluoroacetyl, etc.), amino(lower)alkanoyl (e.g., glycyl, aminopropionyl, diaminobutyryl, etc.), phenyl(lower)alkoxycarbonylamino(lower)alkanoyl (e.g., benzyloxycarbonylglycyl, etc.), phenyl(lower)alkoxycarbonylcarbamoyl (e.g., benzyloxycarbonylcarbamoyl) phenyl(lower)alkoxy(lower)alkanoyl (e.g., benzyloxyacetyl, benzyloxypropionyl, etc.), carboxy(lower)alkanoyl (e.g., carboxyacetyl, carboxypropionyl, etc.), hydroxy(lower)alkanoyl (e.g. glycoloyl, hydroxypropionyl, hydroxybutyryl etc.), etc.

Suitable "higher alkanoyl" moiety in the term "higher alkanoylamino" may be the ones having 8 or more carbon atoms such as octanoyl, nonanoyl, decanoyl, undecanoyl, lauroyl, myristoyl, pentadecanoyl, palmitoyl, heptadecanoyl, stearoyl, icosanoyl, docosanoyl, tetracosanoyl, or the like, preferably ones having 8 to 24 carbon atoms.

Suitable "higher alkoxy" moiety in the terms "higher alkoxycarbonylamino and higher alkoxy(lower)alkanoylamino" may be the ones having 8 or more carbon atoms such as octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy or the like, preferably ones having 12 to 20 carbon atoms.

Suitable "higher alkyl" moiety in the terms "higher alkylaminocarbonylamino and higher alkylthiocarbonylamino" may be the ones having 8 or more carbon atoms such as octyl, nonyl, decyl, undecyl, dodecyl, tridecyl, tetradecyl, pentadecyl, hexadecyl, heptadecyl, octadecyl or the like, preferably ones having 14 to 18 carbon atoms.

Suitable "lower alkanoyl" moiety in the term "higher alkoxy(lower)alkanoylamino" can be referred to the ones as exemplified in the aforesaid definition of "acyl".

Suitable "higher alkenoyl" moiety in the term "higher alkenoylamino" may be the ones having 8 or more carbon atoms such as octenoyl, decenoyl, dodecenoyl, tetradecenoyl, hexadecenoyl, octadecenoyl, icosenoyl, docosenoyl, tetracosenoyl or the like, preferably ones having 20 to 24 carbon atoms.

Suitable example of higher alkoxy(lower)alkanoyl may be the ones having 10 to 17 carbon atoms such as octyloxyacetyl, dodecyloxyacetyl, tridecyloxyacetyl, tetradecyloxyacetyl or the like, preferably ones having 14 to 16 carbon atoms.

The aforesaid "higher alkanoylamino, higher alkenoylamino, higher alkoxycarbonylamino, higher alkylaminocarbonylamino, higher alkoxy(lower)alkanoylamino or higher alkylthiocarbonylamino" may have 1 to 3 suitable substituent(s) such as lower alkyl (e.g., methyl, ethyl, propyl, butyl, pentyl, hexyl, etc.), hydroxy, lower alkanoyloxy (e.g. formyloxy, acetoxy, propionyloxy, butyryloxy, etc.), higher alkanoyloxy (e.g. lauroyloxy, etc.), or the like, and suitable example of said "higher alkanoylamino, higher alkenoylamino, higher alkoxycarbonylamino, higher alkylaminocarbonylamino or higher alkylthiocarbonylamino having substituent(s)" may be lower alkyl-higher alkenoylamino, hydroxy-higher alkanoylamino, lower alkyl-higher alkoxycarbonylamino or (lower or higher) alkanoyloxy-higher alkanoylamino.

Suitable "ar(lower)alkoxy" may include benzyloxy, phenethyloxy, trityloxy; and the like.

Suitable "protected phosphonoxy" may include esterified phosphonoxy in which said ester may be the ones such as lower alkyl ester (e.g. methyl ester, ethyl ester, propyl ester, isopropyl ester, butyl ester, isobutyl ester, t-butyl ester, pentyl ester, t-pentyl ester, hexyl ester, etc.), aryl ester (e.g. phenyl ester, tolyl ester, xylyl ester, mesityl ester, cumenyl ester, etc.), or the like.

The process for preparing the object compounds and starting compounds of the present invention are explained in detail in the following.

PROCESS 1

The compound (Ib) or a salt thereof can be prepared by subjecting the compound (Ia) or a salt thereof to deacylation reaction.

The present deacylation reaction is carried out in accordance with a conventional method such as hydrolysis; reduction; deacylation using Lewis acid; deacylation method by reacting the compound (Ia) with iminohalogenating agent and then with iminoetherifying agent, and, if necessary, subjecting the resulting compound to hydrolysis; or the like.

Suitable iminohalogenating agent may include phosphorus halide (e.g. phosphorus trichloride, phosphorous pentachloride, phosphorus tribromide, phosphorus pentabromide, etc.), phosphorus oxychloride, thionyl chloride, phosgene and the like.

The reaction temperature is not critical, and the reaction is usually carried out under cooling or at ambient temperature.

Suitable iminoetherifying agent reacted with thus obtained reaction product may include an alcohol, metal alkoxide and the like. Suitable alcohol may include alkanol (e.g. methanol, ethanol, propanol, isopropanol, butanol, t-butanol, 1,3-butanediol, etc.) which may be substituted with alkoxy (e.g. methoxy, ethoxy, propoxy, isopropoxy, butoxy, etc.). Suitable metal alkoxide may include alkali metal alkoxide (e.g. sodium alkoxide, potassium alkoxide, etc.), alkaline earth metal alkoxide (e.g. calcium alkoxide, barium alkoxide, etc.) and the like. The reaction temperature is not critical, and the reaction is usually carried out under cooling or at ambient temperature.

Thus obtained product is, if necessary, subjected to hydrolysis. The hydrolysis can readily be carried out by pouring the reaction mixture obtained above into water, but there may be previously added a hydrophilic solvent (e.g. methanol, ethanol, etc.), a base (e.g. alkali metal bicarbonate, trialkylamine, etc.) or an acid (e.g. diluted hydrochloric acid, acetic acid, etc.) to the water.

The reaction temperature is not critical and may be suitably selected in accordance with the kind of the protective group of the amino group and the elimination method as mentioned above, and the present reaction is preferably carried out under a mild condition such as under cooling, at ambient temperature or slightly elevated temperature.

The hydrolysis may include a method using an acid or a base and the like. These methods may be selected depending on the kind of the acyl groups to be eliminated.

Suitable acid may include an organic or an inorganic acid, for example, formic acid, trifluoroacetic acid, benzenesulfonic acid, p-toluenesulfonic acid, hydrochloric acid and the like. The acid suitable for the reaction can be selected according to the kind of acyl group to be eliminated. When the deacylation reaction is conducted with the acid, it can be carried out in the presence or absence of a solvent. Suitable solvent may include an organic solvent, water or a mixed solvent thereof. When trifluoroacetic acid is used, the deacylation reaction may be preferably carried out in the presence of anisole.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-ene, 1,4-diazabicyclo[2,2,2]octane, 1,5-diazabicyclo[5,4,0]undecene-5 or the like. The hydrolysis using a base is often carried out in water or a hydrophilic organic solvent or a mixed solvent thereof.

The reduction may include, for example, reduction with an alkali metal borohydride (e.g. sodium borohydride, etc.), catalytic reduction using conventional catalyst and the like.

The reaction temperature is not critical, and the reaction is usually carried out under cooling to warming. In the present deacylation, the acylamino group(s) of $R^1$, $R^2$, $R^3$ and $R^5$ may be similarly deacylated during the reaction or the post-treatment of the present reaction, which is also included within the scope of the present reaction. The present deacylation reaction further includes, within its scope, the cases that lower or higher alkenoylamino, acyloxy, acylamino substituted with acylamino and acylamino substituted with aryloxy group(s) are converted into the corresponding lower or higher alkanoylamino, hydroxy, acylamino substituted with amino and acylamino substituted with hydroxy respectively, during the reaction or post-treatment of the present process.

PROCESS 2

The object compound (Id) or a salt thereof can be prepared by subjecting the compound (Ic) or a salt thereof to deacylation reaction.

The reaction can be carried out according to a similar manner to that of Process 1.

In this present deacylation reaction, the acylamino group(s) or $R^2$, $R^3$, $R^4$ and $R^5$ may be similarly deacylated during the reaction or the post-treatment of the present reaction, which is also included within the scope of the present reaction.

PROCESS 3

The object compound (If) or a salt thereof can be prepared by subjecting the compound (Ie) or a salt thereof to deacylation reaction.

The reaction can be carried out according to a similar manner to that of Process 1.

In this present deacylation reaction, the acylamino group(s) of $R^1$, $R^3$, $R^4$ and $R^5$ may be similarly deacylated during the reaction or the post-treatment of the present reaction, which is also included within the scope of the present reaction.

PROCESS 4

The object compound (Ig) or a salt thereof can be prepared by reacting the compound (IIb) or its reactive derivative at the amino group or a salt thereof with an acylating agent.

Suitable reactive derivative at the amino group of the compound (IIb) may include silyl derivative formed by the reaction of the compound (IIb) with a silyl compound such as bis(trimethylsilyl)acetamide, mono(trimethylsilyl)acetamide or the like; and the like.

Suitable salt of the compounds (IIb) may include an acid addition salt such as an organic acid salt (e.g. acetate, maleate, tartrate, benzenesulfonate, toluenesulfonate, etc.) or an inorganic acid salt (e.g. hydrochloride, hydrobromide, sulfate, phosphate, etc.) and the like;

Suitable acylating agent may include conventional one and can be shown by the formula: R—OH (III) (wherein) R is acyl as stated above or its reactive derivative at the carboxy group or a salt thereof.

Suitable salt of the compounds (III) may include a metal salt (e.g. sodium salt, potassium salt, calcium salt, magnesium salt, etc.); ammonium salt; an organic amine salt (e.g. triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulforous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl [$(CH_3)_2N^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (III) to be used.

The reaction can preferably be conducted in the present of an organic or inorganic base such as alkali metal (e.g. sodium), alkaline earth metal (e.g. calcium), alkali or alkaline earth metal hydride (e.g. sodium hydride, calcium hydride, etc.), alkali or alkaline earth metal hydroxide (e.g. sodium hydroxide, potassium hydroxide, calcium hydroxide, etc.), alkali or alkaline earth metal carbonate or bicarbonate (e.g. sodium carbonate, potassium carbonate, sodium bicarbonate), alkali or alkaline earth metal alkoxide (e.g. sodium ethoxide, lithium methoxide, magnesium methoxide), trialkylamine (e.g. triethylamine), pyridine, bicyclodiaza compound (e.g. 1,5-diazabicyclo[3,4,0]nonene-5, 1,5-diazabicyclo[5,4,0]undecene-5, etc.) and the like.

When the acylating agent is used in a form of free acid, the reaction of this process may preferably be conducted in the presence of a condensing agent such as carbodiimidic compound (e.g. N,N'-carbonyldiimidazole, N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), N,N-carbonyldi(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus compound (e.g. phosphorus oxychloride, phosphorus trichloride, etc.), thionyl chloride, oxalyl chloride, 2-ethyl-7-hydroxybenzisoxazolium salt, 2-ethyl-5-(m-sulfophenyl)isoxazolium hydroxide, (chloromethylene)dimethylammonium chloride, 2,2,4,4,6,6-hexachloro-1,3,5,2,4,6-triazatriphosphorine, 1-benzenesulphonyloxy-6-chloro-1H-benzotriazole, p-toluenesulfonyl chloride, isopropoxybenzenesulfonyl chloride, or a mixed condensing agent such as triphenylphosphine and a carbon tetrahalide (e.g. carbon tetrachloride, carbon tetrabromide, etc.) or so-called Vilsmeier reagent (e.g. a complex of N,N-dimethylformamide with phosphoryl chloride, phosgene or thionyl chloride).

The reaction is usually conducted in a conventional solvent which does not adversely influence the reaction such as water, acetone, dioxane, acetonitrile, ethyl acetate, N,N-dimethylformamide, dimethylsulfoxide, tetrahydrofuran, dichloromethane, chloroform, pyridine, N-methylmorpholine, N-methylpyrrolidine, etc. or a mixture thereof.

The reaction temperature is not critical and this reaction can be conducted within the temperature range of cooling the heating.

In this present acylation reaction, amino group(s) of $R^2$, $R^3$, $R^4$ and $R^5$ may be similarly acylated during the reaction or the post-treatment of the present reaction, which is also included within the scope of the present reaction.

PROCESS 5

The object compound (Ih) or a salt thereof can be prepared by reacting the compound (IId) or its reactive derivative at the amino group or a salt thereof with an acylating agent.

The reaction can be carried out according to a similar manner to that of Process 4.

In this present acylation reaction, amino group(s) of $R^1$, $R^3$, $R^4$ and $R^5$ may be similarly acylated during the reaction or the post-treatment of the present reaction, which is also included within the scope of the present reaction.

PROCESS 6

The object compound (Ii) or a salt thereof can be prepared by reacting the compound (IIf) or its reactive derivative at the amino group or a salt thereof with an acylating agent.

The reaction can be carried out according to a similar manner to that of Process 4.

In this present acylation reaction, amino group(s) of $R^1$, $R^2$, $R^4$ and $R^5$ may be similarly acylated during the reaction or the post-treatment of the present reaction, which is also included within the scope of the present reaction.

PROCESS 7

The object compound (Ij) or a salt thereof can be prepared by reacting the compound (IIh) or its reactive derivative at the amino group or a salt thereof with an acylating agent.

The reaction can be carried out according to a similar manner to that of Process 4.

In this present acylation reaction, amino group(s) of $R^1$, $R^2$, $R^3$ and $R^5$ may be similarly acylated during the reaction or the post-treatment of the present reaction, which is also included within the scope of the present reaction.

PROCESS 8

The object compound (Il) or a salt thereof can be prepared by reacting the compound (Ik) or its reactive derivative at the amino group or a salt thereof with an acylating agent.

The reaction can be carried out according to a similar manner to that of Process 4.

In this present acylation reaction amino group(s) of $R^2$, $R^3$, $R^4$ and $R^5$ may be similarly acylated during the reaction or the post-treatment of the present reaction, which is also included within the scope of the present reaction.

PROCESS 9

The object compound (In) or a salt thereof can be prepared by reacting the compound (Im) or its reactive derivative at the amino group or a salt thereof with an acylating agent.

The reaction can be carried out according to a similar manner to that of Process 4.

In this present acylation reaction, the amino group(s) of $R^1$, $R^3$, $R^4$ and $R^5$ may be similarly acylated during the reaction or the post-treatment of the present reaction, which is also included within the scope of the present reaction.

PROCESS 10

The object compound (Io) or a salt thereof can be prepared by subjecting the compound (IIm') or a salt thereof to deacylation reaction.

The reaction can be carried out according to a similar manner to that of Process 1.

In this present deacylation reaction, the acylamino group(s) of $R^1$, $R^2$, $R^3$ and $R^4$ may be similarly deacylated during the reaction or the post-treatment of the present reaction, which is also included within the scope of the present reaction.

PROCESS 11

The object compound (Ip) or a salt thereof can be prepared by subjecting the compound (IIq) or a salt thereof to elimination reaction of phosphono protective group.

The reaction can be carried out according to a similar manner to that of basic hydrolysis in Process 1.

In the present reaction, the acylamino group(s) of $R^1$, $R^2$, $R^3$ and $R^4$ may be similarly deacylated during the reaction or the post-treatment of the present reaction, which is also included within the scope of the present reaction.

PROCESS A

The object compound (IIb) or a salt thereof can be prepared by subjecting the compound (IIa) or a salt thereof to deacylation reaction.

The reaction can be carried out according to a similar manner to that of Process 1.

In this present deacylation reaction, the acylamino group(s) of $R^2$, $R^3$, $R^4$ and $R^5$ may be similarly deacylated during the reaction or the post-treatment of the present reaction, which is also included within the scope of the present reaction.

PROCESS B

The object compound (IId) or a salt thereof can be prepared by subjecting the compound (IIc) or a salt thereof to deacylation reaction.

The reaction can be carried out according to a similar manner to that of Process 1.

In this present deacylation reaction, the acylamino group(s) of $R^1$, $R^3$, $R^4$ and $R^5$ may be similarly deacylated during the reaction or the post-treatment of the present reaction, which is also included within the scope of the present reaction.

PROCESS C

The object compound (IIf) or a salt thereof can be prepared by subjecting the compound (IIe) or a salt thereof to deacylation reaction.

The reaction can be carried out according to a similar manner to that of Process 1.

In this present deacylation reaction, the acylamino group(s) of $R^1$, $R^2$, $R^4$ and $R^5$ may be similarly deacylated during the reaction or the post-treatment of the present reaction, which is also included within the scope of the present reaction.

PROCESS D

The object compound (IIh) or a salt thereof can be prepared by subjecting the compound (IIg) or a salt thereof to deacylation reaction.

The reaction can be carried out according to a similar manner to that of Process 1.

In this present deacylation reaction, the acylamino group(s) of $R^1$, $R^2$, $R^3$ and $R^5$ may be similarly deacylated during the reaction or the post-treatment of the present reaction, which is also included within the scope of the present reaction.

PROCESS E

The object compound (IIa) or a salt thereof can be prepared by reacting the compound (IIb) or its reactive derivative at the amino group or a salt thereof with an acylating agent.

The reaction can be carried out according to a similar manner to that of Process 4.

In this present acylation reaction, amino group(s) of $R^2$, $R^3$, $R^4$ and $R^5$ may be similarly acylated during the reaction or the post-treatment of the present reaction, which is also included within the scope of the present reaction.

PROCESS F

The object compound (IIc) or a salt thereof can be prepared by reacting the compound (IId) or its reactive derivative at the amino group or a salt thereof with an acylating agent.

The reaction can be carried out according to a similar manner to that of Process 4.

In this present acylation reaction, amino group(s) of $R^1$, $R^3$, $R^4$ and $R^5$ may be similarly acylated during the reaction or the post-treatment of the present reaction, which is also included within the scope of the present reaction.

PROCESS G

The object compound (IIe) or a salt thereof can be prepared by reacting the compound (IIf) or its reactive derivative at the amino group or a salt thereof with an acylating agent.

The reaction can be carried out according to a similar manner to that of Process 4.

In this present acylation reaction, amino group(s) of $R^1$, $R^2$, $R^4$ and $R^5$ may be similarly acylated during the reaction or the post-treatment of the present reaction, which is also included within the scope of the present reaction.

PROCESS H

The object compound (IIj) or a salt thereof can be prepared by reacting the compound (IIi) or its reactive derivative at the amino group or a salt thereof with an acylating agent.

The reaction can be carried out according to a similar manner to that of Process 4.

In this present acylation reaction, amino group(s) of $R^1$, $R^2$, $R^3$ and $R^4$ may be similarly acylated during the reaction or the post-treatment of the present reaction, which is also included within the scope of the present reaction.

PROCESS I-(1)

The object compound (Il) or a salt thereof can be prepared by subjecting the compound (IIk) or a salt thereof to deacylation reaction.

The reaction can be carried out according to a similar manner to that of Process 1.

In this present deacylation reaction the acylamino group(s) of $R^1$, $R^2$, $R^3$ and $R^4$ may be similarly deacylated during the reaction or the post-treatment of the present reaction, which is also included within the scope of the present reaction.

PROCESS I-(2)

The object compound (IIm) or a salt thereof can be prepared by reacting the compound (III) or its reactive derivative at the amino group or a salt thereof with an acylating agent.

The reaction can be carried out according to a similar manner to that of Process 4.

In this present acylation reaction, amino group(s) of $R^2$, $R^3$ and $R^4$ may be similarly acylated during the reaction or the post-treatment of the present reaction, which is also included within the scope of the present reaction.

PROCESS J-(1)

The object compound (IIn) or a salt thereof can be prepared by subjecting the compound (Io) or a salt thereof to introduction reaction of the hydroxy protective group.

Suitable agent for introduction of the hydroxy protective group may include conventional one and can be shown by the formula: Ra-OH (IIIa) [wherein Ra is ar(lower)alkyl (e.g., benzyl, trityl, etc.)] or its reactive derivative at the hydroxy group or a salt thereof.

The reaction condition can be carried out according to a similar manner to that of Process 4.

PROCESS J-(2)

The object compound (IIo) or a salt thereof can be prepared by reacting the compound (IIn) or a salt thereof with an acylating agent.

The reaction can be carried out according to a similar manner to that of Process 4.

In this present acylation reaction, amino group(s) of $R^1$, $R^2$, $R^3$ and $R^4$ may be similarly acylated during the reaction or the post-treatment of the present reaction, which is also included within the scope of the present invention.

PROCESS J-(3)

The object compound (IIp) or a salt thereof can be prepared by subjecting the compound (IIo) or a salt thereof to elimination reaction of the hydroxy protective group.

The reaction can be carried out according to a similar manner to that of acidic hydrolysis in Process 1.

In this present reaction, the acylamino group(s) of $R^1$, $R^2$, $R^3$ and $R^4$ may be similarly deacylated during the reaction or the post-treatment of the present reaction, which is also included within the scope of the present reaction.

PROCESS J-(4)

The object compound (IIq) or a salt thereof can be prepared by subjecting the compound (IIp) or a salt thereof to introduction reaction of protected phosphono group.

Suitable agent to be used in the present introduction reaction may include diphenyl chlorophosphate and the like.

The reaction is usually conducted in a conventional solvent which does not adversely influence the reaction such as water, acetone, dioxane, acetonitrile, ethyl acetate, N,N-dimethylformamide, dimethylsulfoxide, tetrahydrofuran, dichloromethane, chloroform, pyridine, N-methylmorpholine, N-methylpyrrolidine, etc. or a mixture thereof.

The reaction temperature is not critical and the reaction is usually carried out under cooling, at ambient temperature or under warming.

The object compound (I) and pharmaceutically acceptable salts thereof may be further treated with urea, sugar (e.g. α-cyclodextrin, β-cyclodextrin, γ-cyclodextrin, etc.) or the like, to give a complex with said compounds which are also included within the scope of the present invention.

The object compound (I) and pharmaceutically acceptable salts thereof have antiviral activity and immuno-stimulating activity and therefore, are useful as an antiviral agent for human being, animals and plants and a prophylactic agent for infectious diseases caused by pathogenic microorganisms.

For prophylactic or therapeutic administration, the object compound (I) and the pharmaceutically acceptable salts thereof of the present invention are used in the form of conventional pharmaceutical preparation comprising the same, as active ingredients, in admixture with pharmaceutically acceptable carriers such as an organic or inorganic solid or liquid excipient which is suitable for oral, parenteral and external administration. The pharmaceutical preparations may be in solid form such as tablet, dragee, ointment, granule, powder, capsule or liquid form such as solution, suspension, syrup, emulsion, lemonade and the like. If needed, there may be included in the above preparations auxiliary substances, stabilizing agents, wetting agents and other commonly used additives such as lactose, magnesium stearate, terra alba, sucrose, corn starch, talc, stearic acid, gelatin, agar, pectin, peanut oil, olive oil, cacao butter, ethylene glycol and the like.

While the dosage of the compound (I) or pharmaceutically acceptable salts thereof may vary from and also depend upon the age, conditions of the patient, kinds of diseases, kinds of the compound (I) or pharmaceutically acceptable salts thereof to be applied, etc. In general, preferable dosage of the compound (I) or pharmaceutically acceptable salts thereof to the patient can be selected from 0.1–100 mg/kg/day.

The following Preparations and Examples are given for the purpose of illustrating this invention. In the Examples, it is to be noted that numbering of carbon atom's position of aminoglycoside derivatives is given in accordance with those of Kanamycin A and Kanamycin B as illustrated as follows.

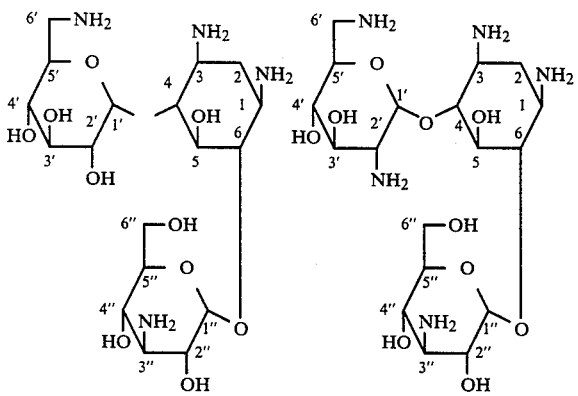

(Kanamycin A)   (Kanamycin B)

In order to illustrate the usefulness of the object compound, anti-viral activity and cytotoxicity of a representative compound of the present invention are shown below.

Assays were carried out in confluent Vero cell cultures in multi-well trays (96 wells). The cell cultures were grown to confluence in Eagle's minimal essential medium (MEM) supplemented with 5% fetal bovine serum (FBS).

(1) Anti-HSV (herpes simplex virus) activity (A) Test Method

The culture medium was changed to 0.5% FBS-MEM. The cell cultures were inoculated with about 100 $TCID_{50}$ of HSV-I Miyama strain, and immediately thereafter, exposed to varying concentrations of the test compound and incubated for 2 days at 37° C. in humidified 5% $CO_2$-95% air. 4 wells were used in each concentrations. They were fixed with 5% trichloroacetic acid and stained with 0.1% crystalviolet. The viral CPE was observed microscopically (×40). Antiviral activity was expressed as $ID_{50}$ (50% inhibitory dose), that is, the concentration of compound required to reduce viral CPE by 50% (within the well), when it had reached completion (100% cell destruction) in the control virus-infected cell cultures.

(B) Test Compound
(1) 1-N-palmitoyl-3''-N-propionylkanamycin A dihydrochloride.
(2) 3''-N-palmitoyl-1-N-trifluoroacetylkanamycin A dihydrochloride.
(3) 1-N-n-hexadecyloxycarbonyl-3''-N-trifluoroacetylkanamycin A dihydrochloride.
(4) 3-N-palmitoyl-3''-N-trifluoroacetylkanamycin A dihydrochloride.
(5) 1-N-n-Icosanoyl-3''-N-trifluoroacetylkanamycin A dihydrochloride.

(C) Test Result

| Compound | Anti-HSV activity (μg/ml) |
|---|---|
| (1) | 1.8 |
| (2) | 2.0 |
| (3) | 2.4 |
| (4) | 2.6 |
| (5) | 2.5 |

(2) Cytotoxicity (A) Test Method

In tests which were run in parallel with the antiviral assays in confluent Vero cell cultures (which had not been infected), the compounds were examined for their effects on normal cell morphology. The cytotoxicity was expressed as the minimum concentration of drug which destroyed the cell monolayer.

(B) Test Compound
(1) 1-N-palmitoyl-3''-N-propionylkanamycin A dihydrochloride.
(2) 3''-N-palmitoyl-1-N-trifluoroacetylkanamycin A dihydrochloride.
(3) 1-N-n-hexadecyloxycarbonyl-3''-N-trifluoroacetylkanamycin A dihydrochloride.
(4) 1-N-n-Icosanoyl-3''-N-trifluoroacetylkanamycin A dihydrochloride.

(c) Test Result

| Compound | Cytotoxicity (μg/ml) |
| --- | --- |
| (1) | 100 |
| (2) | >100 |
| (3) | >100 |
| (4) | >100 |

Preparation 1

To a solution of 3,6'-bis-N-benzyloxycarbonyl-3''-N-trifluoroacetylkanamycin A (1.4 g) in a mixture of tetrahydrofuran (40 ml) and water (10 ml) was dropwise added benzyloxycarbonyl chloride (0.28 ml) under ice-cooling, keeping the pH between 8 and 8.5 with triethylamine and the resultant mixture was stirred at the same temperature for one hour. The reaction mixture was concentrated under reduced pressure. The resultant solid was washed twice with diethyl ether (50 ml) and water (50 ml), in turn and air-dried to give 1,3,6'-tris-N-benzyloxycarbonyl-3''-N-trifluoroacetylkanamycin A (1.45 g).

mp: >260° C. (dec.)

IR (Nujol): 1680, 1645, 1520, 1270, 1150, 1030 cm$^{-1}$

NMR (DMSO-d$_6$, δ): 4.98, 7.28 (15H, s)

Preparation 2

The following compound was obtained according to a similar manner to that of Preparation 1.

1,6'-Bis-N-benzyloxycarbonyl-3-N-tert-butoxycarbonyl-3''-N-trifluoroacetylkanamycin A.

IR (Nujol): 1700, 1680, 1520 cm$^{-1}$

NMR (DMSO-d$_6$, δ): 1.37 (9H, s), 7.33 (10H, s)

Preparation 3

A solution of 1,3,6'-tris-N-benzyloxycarbonyl-3''-N-trifluoroacetylkanamycin A (1.4 g) in a mixture of N,N-dimethylformamide (20 ml) and conc. ammonia (20 ml) was stirred at ambient temperature for 6 hours. An additional conc. ammonia (10 ml) was added to the solution and the mixture was stirred at the same temperature for another 3 hours. The reaction mixture was dropwise added to diethyl ether (150 ml) under stirring. The resultant precipitate was collected by filtration, washed twice with diethyl ether (20 ml) and water (20 ml), and air-dried to give 1,3,6'-tris-N-benzyloxycarbonylkanamycin A (700 mg).

Preparation 4

(a) To a solution of 3,6'-bis-N-benzyloxycarbonyl-3''-N-trifluoroacetylkanamycin A (3 g) in a mixture of tetrahydrofuran (48 ml) and water (12 ml), 2-tert-butoxycarbonyloxyimino-2-phenylacetonitrile (1.04 g) and triethylamine (0.59 ml) were added at ambient temperature and the mixture was stirred at the same temperature for 2 hours. Then 2-tert-butoxycarbonylimino-2-phenylacetonitrile (1.04 g) and triethylamine (0.59 ml) were added to the solution and the mixture was stirred at ambient temperature overnight. The solution was concentrated under reduced pressure to give a residue. The residue was dried under reduced pressure at ambient temperature to give 3,6'-bis-N-benzyloxycarbonyl-1N-tert-butoxycarbonyl-3''-N-trifluoroacetylkanamycin A as a crude solid (12 g).

(b) A solution of 3,6'-bis-N-benzyloxycarbonyl-1-N-tert-butoxycarbonyl-3''-N-trifluoroacetylkanamycin A (crude 12 g) in a mixture of N,N-dimethylformamide (50 ml) and conc. ammonium hydroxide (25 ml) was stirred at ambient temperature overnight. To a solution conc. ammonium hydroxide (15 ml) was added and stirred at ambient temperature for 4 hours. Furthermore, conc. ammonium hydroxide (15 ml) was added to the solution and stirred at the same temperature for 4 hours. The solution was poured into diethyl ether (500 ml) and resultant precipitates were collected by filtration, washed with diethyl ether (100 ml) and water (100 ml). The precipitates were dried under reduced pressure over phosphorus pentoxide to give 3,6'-bis-N-benzyloxycarbonyl-1-N-tert-butoxycarbonylkanamycin A (2.50 g) as a solid.

mp: 246°-7° C.

IR (Nujol): 3320, 1685, 1670 (sh) 1650 (sh), 1520, 1270, 1145, 1065, 1050 cm$^{-1}$ NMR (DMSO-d$_6$, δ): 1.36 (9H, s)

Preparation 5

(1) Phosphorous oxychloride (0.56 ml) was added to a mixture of dimethylformamide (0.47 ml) and tetrahydrofuran (0.9 ml) and the suspension was stirred at −5°-0° C. for 10 minutes. To the above suspension were added tetrahydrofuran (9 ml) and, next, N-(benzyloxycarbonyl)glycin (981 mg) at −5°-0° C. with stirring. The mixture was stirred at the same temperature for 30 minutes to prepare an activated acid solution. To a solution of 3,6'-bis-N-benzyloxycarbonyl-1-N-tert-butoxycarbonylkanamycin A (2 g) in a mixture of tetrahydrofuran (60 ml) and water (15 ml) was dropwise added the activated solution obtained above keeping the pH between 8 and 9 with triethylamine. The reaction mixture was stirred for 30 minutes at the same temperature. The reaction mixture was concentrated under reduced pressure. The resultant solid was collected by filtration, washed in turn with 1N-hydrochloric acid, diethyl ether (90 ml), water until the pH of the washings indicated 7 and a mixture of diethyl ether (10 ml) and iso.propyl alcohol (10 ml), and air-dried to give 3,6'-bis-N-benzyloxycarbonyl-3''-N-[N-benzyloxycarbonyl)glycyl]-1-N-tert-butoxycarbonylkanamycin A (1.91 g) as a solid.

mp: 148°-150° C.

IR (Nujol): 3300, 1680, 1520, 1260, 1150, 1040 cm$^{-1}$

NMR (DMSO-d$_6$, δ): 1.35 (9H, s)

(2) To a solution of 3,6'-bis-N-benzyloxycarbonyl-1-N-tert-butoxycarbonylkanamycin A (2 g) in a mixture of tetrahydrofuran (40 ml) and water (10 ml), acetyl chloride (0.22 g) was dropwise added with stirring at ambient temperature, keeping the pH between 8 and 8.5 with triethylamine. The solution was stirred at the same temperature for one hour. The resultant precipitates were collected by filtration and the precipitate was three times washed with diethyl ether (20 ml) and water (60 ml) in turn. The precipitate was air-dried to give 3''-N-acetyl-3,6'-bis-N-benzyloxycarbonyl-1-N-tert-butoxycarbonylkanamycin A as a solid (1.86 g).

mp: >236° C. (dec.)

IR (Nujol): 1680, 1510, 1500, 1140, 1030 cm$^{-1}$

NMR (DMSO-d$_6$, δ): 1.85 (3H, s)

Preparation 6

The following compounds were obtained according to a similar manner to those of Preparation 5 (1) and 5 (2).

(1) 3''-N-benzyloxyacetyl-3,6'-bis-N-benzyloxycarbonyl-1-N-tert-butoxycarbonylkanamycin A.

IR (Nujol): 1680, 1520 cm$^{-1}$

NMR (DMSO-d$_6$, δ): 1.37 (1H, s), 4.57 (2H, s), 7.27 (5H, s), 7.30 (5H, s), 7.33 (5H, s)

(2) 3,6',3''-Tris-N-benzyloxycarbonyl-1'-N-tert-butoxycarbonylkanamycin A.

mp: >239° C. (dec.)

IR (Nujol): 3320, 1690, 1520, 1300, 1150, 1070, 1040 cm$^{-1}$

NMR (DMSO-d$_6$, δ): 1.35 (9H, s), 5.00 (6H, s), 7.31 (10H, s)

Preparation 7

A solution of 3,6',3''-tris-N-benzyloxycarbonyl-1-N-tert-butoxycarbonylkanamycin A (1 g) in a mixture of anisole (3 ml) and trifluoroacetic acid (10 ml) was stirred under ice-cooling for 30 minutes. The solution was concentrated under reduced pressure to give a residue. Diethyl ether (50 ml) was poured into the residue. The resultant precipitate was collected by filtration and washed with diethyl ether (30 ml) three times. Then the precipitate was dried over phosphorus pentoxide under reduced pressure for 2 hours to give 3,6',3''-tris-N-benzyloxycarbonylkanamycin A mono-trifluoroacetate (901 mg).

IR (Nujol): 3300–3250, 1690, 1540–1510, 1080, 1050 cm$^{-1}$

NMR (DMSO-d$_6$, δ): 5.00, 7.30 (15H, s)

Preparation 8

A solution of 6'-N-benzyloxycarbonylkanamycin A (4.19 g) and zinc acetate dihydrate (6.54 g) in dimethylsulfoxide (140 ml) was stirred overnight. 2-(Tert-butoxycarbonyloxyimino)-2-phenylacetonitrile (1.83 g) and triethylamine (1.04 ml) were added to the solution at ambient temperature. The mixture was stirred at the same temperature overnight. The mixture was poured into diethyl ether (3 l). The supernatant solution was removed by decantation to give a syrup. The syrup was triturated twice with diethyl ether and dissolved in a mixture of 1,4-dioxane (100 ml) and water (100 ml). This solution was passed through a column of cation exchange resin, Amberlite ®IRC-50 (H+ type trade mark maded by Rhom and Haas Co.) (200 ml), and eluted with 50% aqueous 1,4-dioxane (600 ml) and 1N ammonia in 50% aqueous 1,4-dioxane. The fractions containing the desired compound were combined and concentrated in vacuo. The residue was dissolved in a mixture of ethanol and toluene. The solvent was completely concentrated in vacuo to give 6'-N-benzyloxycarbonyl-3-N-tert-butoxycarbonylkanamycin A (3.98 g).

NMR (DMSO-d$_6$, δ): 1.33 (9H, s), 7.27 (5H, s)

Preparation 9

To a solution of 6'-N-benzyloxycarbonyl-3-N-tert-butoxycarbonylkanamycin A (3.9 g) in a mixture of tetrahyrofuran (40 ml) and water (7 ml) was added benzyloxycarbonyl chloride (1.7 ml) under ice-cooling, keeping the pH between 8 and 9 with triethylamine. The mixture was stirred under the same condition for one hour. The mixture was concentrated in vacuo to give a solid, which was washed with water and dried over phosphorus pentoxide in vacuo to give 1,6',3''-tris-N-benzyloxycarbonyl-3-N-tert-butoxycarbonylkanamicin A (5.15 g).

IR (Nujol): 1680, 1520 cm$^{-1}$

NMR (DMSO-d$_6$, δ): 1.37 (9H, s), 7.33 (15H, s)

Preparation 10

To a suspension of 1,6',3''-tris-N-benzyloxycarbonyl-3-N-tert-butoxycarbonylkanamycin A (987 mg) in anisole (3 ml) was added trifluoroacetic acid (10 ml) under ice-cooling. The mixture was stirred under ice-cooling for 3 hours and at ambient temperature for 2 hours. The mixture was concentrated in vacuo to a residue. Toluene was added to the residue and the mixture was concentrated in vacuo. The mixture of the residue and silica gel (2 g) in tetrahydrofuran was concentrated in vacuo. The resultant powder was subjected to column chromatography on silica gel (30 g) and eluted with a mixture chloroform and methanol (10:1 (V/V), next 8:2 (V/V)). The fractions containing the desired compound were combined and concentrated in vacuo to give 1,6',3''-tris-N-benzyloxycarbonylkanamycin A (309 mg).

IR (Nujol): 1670, 1510 cm$^{-1}$

NMR (DMSO-d$_6$, δ): 7.33 (s)

Preparation 11

To a solution of 6'-N-benzyloxycarbonyl-3-N-tert-butoxycarbonylkanamycin A (2.69 g) in dimethylsulfoxide (25 ml) was added ethyl trifluoroacetate (693 mg) at ambient temperature and the mixture was stirred for 30 minutes. The mixture was poured into diethyl ether (500 ml) to give a precipitate. The precipitate was collected, washed with diethyl ether and water in turn, and dried over phosphorus pentoxide in vacuo to give 6'-N-benzyloxycarbonyl-3-N-tert-butoxycarbonyl-3''-N-trifluoroacetylkanamycin A (2.84 g).

IR (Nujol): 1700–1670, 1520 cm$^{-1}$

NMR (DMSO-d$_6$, δ): 1.37 (9H, s), 7.33 (5H, s)

Preparation 12

To a solution of crude 6'-N-benzyloxycarbonyl-1,3,3''-tris-N-tert-butoxycarbonylkanamycin A (2.15 g) in pyridine (22 ml) was added acetic anhydride (2.64 ml) at ambient temperature and the mixture was stirred at the same temperature overnight. An additional acetic anhydride (2.6 ml) was added to the mixture and the mixture was stirred for another 4 hours. Methanol (10 ml) was added to the reaction mixture at ambient temperature to decompose the excess acetic anhydride and the mixture was concentrated in vacuo. The residue, dissolved in ethyl acetate, was washed with water, 2N-sulfuric acid, and water in turn, dried over magnesium sulfate, and concentrated. The resultant residue was purified by column chromatography on silica gel (70 g) (eluent:chloroform and methanol 100:1 (V/V)). The fractions containing the desired compound were collected and concentrated in vacuo to give 2',3',4',2'',4'',6''-hexa-O-acetyl-6'-N-benzyloxycarbonyl-1,3,3''-tris-N-tert-butoxycarbonylkanamycin A (1.46 g).

IR (Nujol): 1750–1700, 1510 cm$^{-1}$

NMR (CDCl$_3$, δ): 1.43, 2.03–2.30, 7.33

Preparation 13

The following compound was obtained according to a similar manner to that of Preparation 12.

2',3',4',2'',4'',6''-Hexa-O-acetyl-3''-N-acetyl-3,6'-bis-N-benzyloxycarbonyl-1-N-tert-butoxycarbonylkanamycin A.

IR (Nujol): 3330, 1740, 1520, 1240, 1170, 1040 cm$^{-1}$

NMR (CDCl$_3$, δ): 1.32 (9H, s), 1.90–2.20 (21H)

Preparation 14

A solution of 2',3',4',2'',4'',6''-hexa-O-acetyl-3''-N-acetyl-3,6'-bis-N-benzyloxycarbonyl-1-N-tert-butoxycarbonylkanamycin A (2.5 g) in a mixture of trifluoroacetic acid (30 ml) and anisole (7 ml) was stirred under ice-cooling for one hour. The reaction mixture was concentrated under reduced pressure to give a residue containing 2',3',4',2'',4'',6''-hexa-O-acetyl-3''-N-acetyl-3,6'-bis-N-benzyloxycarbonylkanamycin A.

(b) Phosphorus oxychloride (0.29 ml) was added to a mixture of dimethylformamide (0.25 ml) and tetrahydrofuran (0.5 l) and to the resultant suspension were added successively tetrahydrofuran (5 ml), and, 3-acetoxytetradecanoic acid (706 mg) at −5°–0° C. with stirring. The mixture was stirred at the same temperature for 30 minutes to prepare an activated acid solution. The solution of the intermediate obtained above in a mixture of tetrahydrofuran (40 ml) and water (10 ml), was dropwise added to the activated acid solution keeping the pH between 8 and 9 with triethylamine. The mixture was stirred for 30 minutes at the same temperature. The reaction mixture was concentrated under reduced pressure. The residue was dissolved in ethyl acetate (120 ml) and the solution was washed with aqueous sodium bicarbonate and water, dried over anhydrous sodium sulfate, and concentrated under reduced pressure. The residue was subjected to column chromatography on silica gel (50 g) and eluted with a mixture of chloroform and methanol (30:1 V/V).

Fractions containing the object compound were combined and concentrated under reduced pressure to give 2',3',4',2'',4'',6''-hexa-O-acetyl-3''-N-acetyl-1-N-(3-acetoxytetradecanoyl)-3,6'-bis-N-benzyloxycarbonylkanamycin A (1.95 g).

IR (Nujol): 3270, 1720–1700, 1650, 1530–1510, 1060–1020 cm$^{-1}$

NMR (CDCl$_3$, δ): 2.88 (3H, m)

Preparation 15

To a solution of 2',3',4',2'',4'',6''-hexa-O-acetyl-6'-N-benzyloxycarbonyl-1,3,3''-tris-N-tert-butoxycarbonylkanamycin A (1.41 g) in methanol (28 ml) was added potassium hydroxide (811 mg) at ambient temperature. The mixture was stirred at the same temperature for 2 hours. Water (75 ml) was added to the mixture. The resultant precipitate was filtered off, washed with water and dried over phosphorus pentoxide in vacuo to give 6'-N-benzyloxycarbonyl-1,3,3''-tris-N-tert-butoxycarbonylkanamycin A (1.04 g).

IR (Nujol): 1670, 1520 cm$^{-1}$

NMR (DMSO-d$_6$, δ): 1.33 (27H, s), 7.33 (5H, s)

Preparation 16

To a solution of 6'-N-benzyloxycarbonylkanamycin A (1.5 g) in a mixture of 1,4-dioxane (20 ml) and water (10 ml) were added 2-(tert-butoxycarbonyloxyimino)-2-phenylacetnitrile (3.58 g) and triethylamine (2 ml) at ambient temperature. The mixture was stirred overnight. The reaction mixture was concentrated to give a solid, which was washed with diethyl ether to give crude 6'-N-benzyloxycarbonyl-1,3,3''-tris-N-tert-butoxycarbonylkanamycin A (2.16 g).

Preparation 17

To a solution of 3,2',6'-tris-N-benzyloxycarbonyl-3',4'-dideoxy-3''-N-trifluoroacetylkanamycin B (2.0 g) in a mixture of tetrahydrofuran (30 ml) and water (7 ml) was added a mixture of 2-(tert-butoxycarbonyloxyimino)-2-phenylacetonitrile (1.03 g) and triethylamine (0.59 ml) at ambient temperature. The mixture was stirred at ambient temperature overnight. The reaction mixture was concentrated in vacuo. To the solution of the resultant residue in N,N-dimethylformamide (30 ml) was added conc. aqueous ammonia (30 ml) at ambient temperature and the mixture was stirred overnight. The resultant mixture was concentrated in vacuo. To the residue, dissolved in N,N-dimethylformamide (30 ml) was added conc. aqueous ammonia (10 ml) at ambient temperature. The mixture was stirred again overnight at ambient temperature. The mixture was concentrated in vacuo to dry up. The residue, washed with diethylether was dissolved in a mixture of tetrahydrofuran (40 ml) and water (10 ml). To the resulting solution was added benzyloxycarbonyl chloride (0.31 ml) under ice-cooling, keeping the pH between 7 and 8 with triethylamine. The resultant mixture was stirred under the same condition for one hour. From the reaction mixture, tetrahydrofuran was removed by evaporation. The resultant precipitate was collected by filtration washed with water, and dried over phosphorus pentoxide. The suspension of the precipitate in anisole (5.5 ml) was added to trifluoroacetic acid (18.3 ml) under ice-cooling. The mixture was stirred for one hour under ice-cooling. The mixture was concentrated in vacuo. The residue was completely dried up by co-evaporation with toluene. The residue was subjected to column chromatography on silica gel (45 g) eluting with a mixture of chloroform and methanol (10:1) and then with a mixture of chloroform and methanol (4:1). The first fraction was concentrated in vacuo to give 3,2',6',3''-tetrakis-N-benzyloxycarbonyl-3',4'-dideoxykanamycin B (303 mg).

IR (CHCl$_3$): 1680, 1510 cm$^{-1}$

Preparation 18

The following compounds were obtained according to a similar manner to that of Preparation 7.
(1) 3,6'-Bis-N-benzyloxycarbonyl-3''-N-[N-(benzyloxycarbonyl)glycyl]kanamycin A.
(2) 3''-N-acetyl-3,6'-bis-N-benzyloxycarbonylkanamycin A.
(3) 3''-Benzyloxyacetyl-3,6'-bis-N-benzyloxycarbonylkanamycin A.
(4) 3,6'-Bis-N-benzyloxycarbonyl-3''-N-[N-(benzyloxycarbonyl)glycyl]kanamycin A monotrifluoroacetate.

Preparation 19

The following compound was obtained according to a similar manner to that of Preparation 10.
1,6'-Bis-N-benzyloxycarbonyl-3''-N-trifluoroacetylkanamycin A.

Preparation 20

To a solution of hexadecanethiol (3 g) in absolute dichloromethane (50 ml) and pyridine (1.9 ml) was added p-nitrophenyl chloroformate (2.57 g) under ice-cooling. The reaction mixture was stirring at the same temperature for an hour and then at ambient temperature overnight. The solution was washed with 1N-hydrochloric acid, water, and saturated aqueous sodium chloride, in turn, dried over sodium sulfate, and concentrated under reduced pressure to give p-nitrophenyl S-hexadecylthiocarbonate (5.04 g) as a solid.

IR (Nujol): 1705, 1620, 1590, 1530, 1490, 1350, 1195, 1160, 1120 cm$^{-1}$

Preparation 21

(1) To a solution of 3,6''-bis-N-benzyloxycarbonyl-1-N-palmitoyl-3''-N-trifluoroacetylkanamycin A (1 g) in pyridine (20 ml) was added trityl chloride (0.77 g) at ambient temperature and the mixture was stirred at 70° C. for 4 hours. The reaction mixture was concentrated under reduced pressure to give a residue, which was washed three times with n-hexane (20 ml) and dried under reduced pressure. The resultant residue was dissolved in pyridine (20 ml) and to the solution was added acetic anhydride (3 ml) with stirring at ambient temperature. The mixture was allowed to stand at ambient temperature overnight. The reaction mixture was concentrated under reduced pressure to give a residue. The residue was dissolved in ethyl acetate (50 ml) and the solution was washed with 1N-hydrochloric acid, aqueous sodium hydrogen carbonate, and aqueous sodium chloride, dried over anhydrous sodium sulfate, and concentrated under reduced pressure to give a residue. The residue was subjected to column chromatography on silica gel (60 g) and eluted with a mixture of chloroform and methanol (100:1 v/v). Fractions containing the object compound were collected and concentrated under reduced pressure to give 2′,3′,4′,2″,4″-penta-O-acetyl-3,6′-bis-N-benzyloxycarbonyl-1-N-palmitoyl-3″-N-trifluoroacetyl-6″-O-tritylkanamycin A (693 mg).

IR (Nujol): 1740, 1720, 1520, 1220, 1150, 1030 cm$^{-1}$

NMR (CDCl$_3$, δ): 0.91 (3H, m), 1.70 (3H, s), 1.74 (3H, s), 1.99 (3H, s), 2.00 (3H, s), 2.10 (3H, s).

(2) A solution of 2′,3′,4′,2″,4″-penta-O-acetyl-3,6-bis-N-benzyloxycarbonyl-1-N-palmitoyl-3″-N-trifluoroacetyl-6″-O-tritylkanamycin A (653 mg) in a mixture of acetic acid (16 ml) and water (4 ml) was stirred at 80° C. for 2 hours. The reaction mixture was concentrated under reduced pressure to give a residue. The residue was triturated with n-hexane (20 ml). The resultant precipitate were collected by filtration and air-dried to give 2′,3′,4′,2″,4″-penta-O-acetyl-3,6′-bis-N-benzyloxycarbonyl-1-N-palmitoyl-3″-N-trifluoroacetylkanamycin A (500 mg).

NMR (DMSO-d$_6$, δ): 1.90 (15H, m).

(3) A solution of 2′,3′,4′,2″,4″-penta-O-acetyl-3,6′-bis-N-benzyloxycarbonyl-1-N-palmitoyl-3″-N-trifluoroacetylkanamycin A (1 g), 1-methylimidazole (278 mg), and diphenyl chlorophosphate (455 mg) in dioxane (20 ml) was stirred under ice-cooling for 10 minutes and then at ambient temperature for 2 hours. The reaction mixture was concentrated under reduced pressure to give a residue, whose solution in ethyl acetate (60 ml) was washed with saturated aqueous sodium bicarbonate and saturated aqueous sodium chloride, dried over sodium sulfate, and concentrated under reduced pressure. The residue was subjected to column chromatography on silica gel (50 g) eluting with a mixture of chloroform and methanol (40:1 v/v). Fractions containing the object compound were collected and concentrated under reduced pressure to afford 2′,3′,4′,2″,4″-penta-O-acetyl-3,6′-bis-N-benzyloxycarbonyl-6″-O-(diphenylphosphoryl)-1-N-palmitoyl-3″-N-trifluoroacetylkanamycin A (453 mg).

IR (Nujol+EtOH): 1740, 1710, 1645, 1520, 1210 cm$^{-1}$

NMR (CDCl$_3$, δ): 0.90 (3H, m), 1.75 (3H, s), 1.95 (3H, s), 2.00 (3H, s), 2.02 (3H, s), 2.10 (3H, s), 7.10–7.50 (20H, m).

Preparation 22

The following compound was obtained according to a similar manner to that of Preparation 12.

2′,3′,4′,2″,4″,6″-Hexa-O-acetyl-3,6′-bis-N-benzyloxycarbonyl-1-N-n-pentadecanoyl-3″-N-trifluoroacetylkanamycin A.

IR (Nujol): 3200, 1745, 1720, 1690, 1640, 1530, 1230, 1165, 1040 cm$^{-1}$

NMR (CDCl$_3$, δ): 0.92 (3H, m), 1.90–2.15 (18H)

Preparation 23

A solution of 3,6′-bis-N-benzyloxycarbonyl-3″-N-(N-benzyloxycarbonylglycyl)kanamycin A trifluoroacetate (8.6 g) in methanol (50 ml) was adjusted to pH 8–9 with 1N aqueous solution of potassium carbonate. The mixture was poured into water (200 ml) and the resultant precipitates were collected by filtration, washed with water, and air-dried to give 3,6′-bis-N-benzyloxycarbonyl-3″-N-(N-benzyloxycarbonylglycyl)kanamycin A (4.45 g).

IR (Nujol): 3320, 1690, 1540, 1270, 1155, 1050 cm$^{-1}$

Example 1

(1) A suspension of 3,6′-bis-N-benzyloxycarbonyl-3″-N-palmitoyl-1-N-trifluoroacetylkanamycin A (650 mg) in a mixture of methanol (10 ml) and 1N-hydrochloric acid (2 ml) was hydrogenated under 1 atmospheric pressure of hydrogen in the presence of palladium black (650 mg) at ambient temperature for 2.5 hours. The catalyst was filtered and washed with water. The filtrate and washings were combined and lyophilized to give 3″-N-palmitoyl-1-N-trifluoroacetylkanamycin A dihydrochloride (503 mg).

mp: 193° C. (dec.)

IR (Nujol): 1700, 1620, 1550 cm$^{-1}$

NMR (CD$_3$OD, δ): 0.87–1.07 (3H, m), 5.03 (1H, d, J=3 Hz), 5.50 (1H, d, J=3 Hz)

FD Mass: 819 (M+), 723 (M+ −96)

(2) A solution of 3″-acryloyl-3,6′-bis-N-benzyloxycarbonyl-1-N-palmitoylkanamycin A (491 mg) in a mixture of methanol (20 ml), tetrahydrofuran (10 ml) and conc. hydrochloric acid (0.5 ml) was hydrogenated under atmospheric pressure of hydrogen at ambient temperature for 5 hours in the presence of 10% palladium on carbon (500 mg). The catalyst was concentrated under reduced pressure to give a residue. The residue was dissolved in water (30 ml) and the solution was treated with activated carbon (200 mg) and filtered off. The filtrate was lyophilized to give 1-N-palmitoyl-3″-N-propionylkanamycin A dihydrochloride (292 mg).

mp: >134° C. (dec.)

[α]$_D^{20}$: 49.2° (C1.0 H$_2$O)

IR (Nujol): 1630, 1540, 1140, 1020 cm$^{-1}$

NMR (CD$_3$OD, δ): 5.06 (1H, d, J=3 Hz)

FD Mass: 779 (M+)

Example 2

The following compounds were obtained according to a similar manner to those of Example 1(1) and 1(2).

(1) 1-N-n-Docosanoyl-3″-N-trifluoroacetylkanamycin A dihydrochloride.

mp: >223° C. (dec.)

[α]$_D^{20}$: 39.3° (C1.0, H$_2$O)

IR (Nujol): 3300, 1700, 1630, 1550, 1160, 1030 cm$^{-1}$

NMR (CD$_3$OD, δ): 0.92 (3H, m), 5.13 (1H, d, J=4 Hz)

(2) 1-N-n-Pentadecanoyl-3″-trifluoroacetylkanamycin A.

mp: >176° C.

[α]$_D^{20}$: +59.8° (C1.0 H$_2$O)

IR (Nujol): 1700, 1630, 1560, 1160, 1030 cm$^{-1}$

NMR (CD$_3$OD, δ): 5.13 (1H, d, J=4 Hz), 5.52 (1H, d, J=3 Hz)

FD Mass: 805 (M+)

(3) 1-N-(2-Hexyldecanoyl)-3″-N-trifluoroacetylkanamycin A dihydrochloride.

mp: >183° C. (dec.)

[α]$_D^{20}$: +82.2° (C1.0, H$_2$O)

IR (Nujol): 1700, 1630, 1160, 1030 cm$^{-1}$
NMR (CD$_3$OD, δ): 5.17 (1H, d, J=3.5 Hz)
FD Mass: 819 (M+)

(4) 1-N-(3-Acetoxy-n-tetradecanoyl)-3''-N-trifluoroacetylkanamycin A dihydrochloride.
mp: >163° C. (dec.)
$[α]_D^{20}$: 59.4° (C1.0, H$_2$O)
IR (Nujol): 3250, 1700, 1640, 1560, 1155, 1025 cm$^{-1}$
NMR (CD$_3$OD, δ): 2.03 (3H, s)

(5) 1-N-(3-Hydroxytetradecanoyl)-3''-N-trifluoroacetylkanamycin A dihydrochloride.
mp: >116° C. (dec.)
$[α]_D^{20}$: +63.8° (C1.0, H$_2$O)
IR (Nujol): 1700, 1630, 1560, 1150, 1030 cm$^{-1}$
NMR (CD$_3$OD, δ): 5.13 (1H, d, J=3 Hz), 5.25 (1H, d, J=3 Hz)
FD Mass: 807 (M+)

(6) 1-N-(3-Acetoxy-n-tetradecanoyl)kanamycin A trihydrochloride.
mp: >153° C. (dec.)
$[α]_D^{20}$: 66.0° (C1.0, H$_2$O)
IR (Nujol): 1710, 1640, 1500, 1260–1240, 1140 cm$^{-1}$
NMR (CD$_3$OD, δ): 2.00 (3H, s), 5.43 (1H, d, J=3 Hz)

(7) 3''-N-Acetyl-1-N-(3-hydroxy-n-tetradecanoyl)kanamycin A dihydrochloride.
mp: >113° C. (dec.)
$[α]_D^{20}$: 71.8° (C1.0, H$_2$O)
IR (Nujol): 1630, 1560, 1140, 1030 cm$^{-1}$
NMR (CD$_3$OD, δ): 2.10 (3H, s), 5.45 (1H, d, J=4 Hz)

(8) 3''-N-Acetyl-1-N-palmitoylkanamycin A dihydrochloride.
mp: >193° C. (dec.)
$[α]_D^{20}$: 74.5° (C1.0, H$_2$O)
IR (Nujol): 1630, 1540, 1025 cm$^{-1}$
NMR (D$_2$O, δ): 0.83 (3H, m), 1.23 (28H, s), 2.02 (3H, s)
FD Mass: 765 (M+)

(9) 3''-N-Benzoyl-1-N-palmitoylkanamycin A dihydrochloride.
mp: >166° C. (dec.)
$[α]_D^{20}$ +62.5° (C1.0, H$_2$O)
IR (Nujol): 1630, 1550, 1140, 1080, 1030 cm$^{-1}$
NMR (CD$_3$OD, δ): 5.25 (1H, d, J=4 Hz) 7.35–8.00 (5H, m)
FD Mass: 828 (M++1)

(10) 3''-N-(3-Carboxypropionyl)-1-N-palmitoylkanamycin A dihydrochloride.
mp: >145° C. (dec.)
$[α]_D^{20}$: +54.0° (C1.0, H$_2$O)
IR (Nujol): 3250, 1720, 1640, 1550, 1140, 1030 cm$^{-1}$
NMR (CD$_3$OD, δ): 2.60 (4H, s), 5.50 (1H, d, J=3 Hz)

(11) 1-N-(3-Acetoxytetradecanoyl)-3''-N-glycylkanamycin A trihydrochloride.
mp: >161° C. (dec.)
$[α]_D^{20}$: 49.2° (C1.0, H$_2$O)
IR (Nujol): 1630, 1560, 1300, 1250, 1025 cm$^{-1}$
NMR (CD$_3$OD, δ): 2.00 (3H, s)
FD Mass: 810 (M+)

(12) 3''-N-Glycyl-1-N-palmitoylkanamycin A trihydrochloride.
mp: >163° C. (dec.)
IR (Nujol): 1620, 1560, 1300, 1140, 1080, 1030 cm$^{-1}$
NMR (CD$_3$OD, δ): 0.97 (3H, m), 1.30 (28H, s)
FD Mass: 780 (M+)
$[α]_D^{20}$: 47.6° (C1.0, H$_2$O)

(13) 1-N-Acetyl-3''-N-palmitoylkanamycin A dihydrochloride.
mp: 168° C. (dec.)
$[α]_D^{26}$: +72.7° (C=0.74, H$_2$O)
IR (Nujol): 1630, 1550 cm$^{-1}$
NMR (CD$_3$OD, δ): 0.87 (3H, m), 1.97 (3H, s), 5.07 (1H, d, J=3 Hz), 5.47 (1H, d, J=3 Hz)
FD Mass: 765 (M+)

(14) 3''-N-Glycoloyl-1-N-palmitoylkanamycin A dihydrochloride.
mp: 159° C. (dec.)
$[α]_D^{26}$: +73.2 (C=0.55, H$_2$O)
IR (Nujol): 1640, 1550 cm$^{-1}$
NMR (CD$_3$OD, δ): 5.10 (1H, d, J=3 Hz), 5.47 (1H, m)
FD Mass: 803 (M++22)

(15) 1,3''-Bis-N-n-octanoylkanamycin A dihydrochloride.
mp: 197° C. (dec.)
IR (Nujol): 1640, 1550 cm$^{-1}$
NMR (CD$_3$OD, δ): 0.90 (6H, t, J=5 Hz), 5.07 (1H, d, J=3 Hz), 5.47 (1H, d, J=3 Hz)
FD Mass: 737 (M+)

(16) 1-N-tert-Butoxycarbonyl-3''-N-palmitoylkanamycin A dihydrochloride.
mp: 192° C. (dec.)
IR (Nujol): 1680, 1640, 1540 cm$^{-1}$
NMR (CD$_3$OD, δ): 0.87–1.03 (3H, m), 1.47 (9H, s), 5.10 (1H, d, J=3 Hz), 5.43–5.57 (1H, m)
FD Mass: 823 (M+), 723 (M+ −100)

(17) 1-N-n-Tridecyloxyacetyl-3''-N-trifluoroacetylkanamycin A dihydrochloride.
mp: 173° C. (dec.)
$[α]_D^{26}$: +65.1 (C=0.34, H$_2$O)
IR (KBr): 1700, 1650, 1560 cm$^{-1}$
NMR (CD$_3$OD, δ): 0.90–1.03 (3H, m), 5.07 (1H, d, J=3 Hz), 5.47–5.53 (1H, m)
FD Mass: 843 (M++22), 821 (M+), 747 (M+−74), 725 (M+−96)

(18) 1-N-n-hexadecyloxycarbonyl-3''-N-trifluoroacetylkanamycin A dihydrochloride.
mp: >156° C. (dec.)
IR (Nujol): 3300, 1700, 1560–1540, 1510, 1270, 1155, 1080, 1030 cm$^{-1}$
NMR (CD$_3$OD, δ): 0.95 (3H, m), 5.12 (1H, d, J=3 Hz), 5.48 (1H, d, J=3 Hz)

(19) 1-N-n-hexadecylthiocarbonyl-3''-N-trifluoroacetylkanamycin A dihydrochloride.
mp: >213° C. (dec.)
IR (Nujol): 3300–3250, 1705, 1635, 1520, 1210, 1160 cm$^{-1}$
NMR (CD$_3$OD, δ): 0.95 (3H, m), 5.13 (1H, d, J=3 Hz), 5.48 (1H, d, J=3 Hz)
FD Mass: 864 (M+−1)

(20) 1-N-n-pentadecylaminocarbonyl-3''-N-trifluoroacetylkanamycin A dihydrochloride.
mp: 135° C. (dec.)
IR (Nujol): 1705, 1570, 1210, 1185, 1160, 1030 cm$^{-1}$
NMR (CD$_3$OD, δ): 0.93 (3H, m), 5.12 (1H, d, J=3 Hz), 5.47 (1H, d, J=3 Hz)

Example 3

A suspension of 1,6'-bis-N-benzyloxycarbonyl-3-N-palmitoyl-3''-N-trifluoroacetylkanamycin A (800 mg) in a mixture of methanol (8 ml) and 1N-hydrochloric acid (2 ml) was hydrogenated under 1 atmospheric pressure of hydrogen in the presence of palladium black (400 mg) at ambient temperature for 6 hours. The catalyst was filtered and washed with water. The filtrate and washings were combined and lyophilized to give 3-N-palmitoyl-3''-N-trifluoroacetylkanamycin A dihydrochloride (627 mg).
mp: 181° C. (dec.)
IR (Nujol): 1710, 1620, 1550 cm$^{-1}$ NMR (CD₃OD, δ): 0.87–1.03 (3H, m), 5.10 (1H, d, J=3 Hz), 5.40 (1H, d, J=3 Hz)
FD Mass: 819 (M+), 723 (M+ −96)

Example 4

A suspension of 3,2′,6′-tris-N-benzyloxycarbonyl-1-N-palmitoyl-3″-N-trifluoroacetylkanamycin B (510 mg) in a mixture of methanol (10 ml) and 1N-hydrochloric acid (1.5 ml) was hydrogenated under 1 atmospheric pressure of hydrogen in the presence of palladium black (500 mg) at ambient temperature for 5 hours. The catalyst was filtered and washed with water. The filtrate and washings were combined and lyophilized to give 1-N-palmitoyl-3″-N-trifluoroacetylkanamycin B trihydrochloride (312 mg).

mp: 220° C. (dec.)
$[\alpha]_D^{26}$: +69.8° (C=0.65, H₂O)
IR (Nujol): 1700, 1630, 1550 cm⁻¹
NMR (CD₃OD, δ): 0.90–1.08 (3H, m), 5.08 (1H, d, J=3 Hz), 5.43–5.53 (1H, m)
FD Mass: 819 (M+ +1), 722 (M+ −96), 6.58 (M+ −160), 562 (M+ −256)

Example 5

The following compound was obtained according to a similar manner to that of Example 4.

3′,4′-Dideoxy-1-N-palmitoyl-3″-N-trifluoroacetylkanamycin B trihydrochloride.

mp: 206° C. (dec.)
$[\alpha]_D^{26}$: +55.67° (C=0.347, H₂O)
IR (Nujol): 1700, 1630 cm⁻¹
FD Mass: 809 (M+ +23), 808 (M+ +22), 787 (M+ +1), 713 (M+ −73), 691 (M+ −95)

Example 6

A solution of 3,2′,6′,3″-tetrakis-N-benzyloxycarbonyl-3′,4′-dideoxy-1-N-palmitoylkanamycin B (300 mg) in a mixture of methanol (12 ml) and 1N-hydrochloric acid (0.9 ml) was hydrogenated under 1 atmospheric pressure of hydrogen in the presence of palladium black (300 mg) at ambient temperature for 7 hours. The catalyst was filtered off and washed with aqueous methanol. The filtrate and washings were combined and lyophilized to give 3′,4′-dideoxy-1-N-palmitoylkanamycin B tetrahydrochloride (183 mg).

mp: 167° C. (dec.)
$[\alpha]_D^{26}$: +63.49° (C=0.158, H₂O)
IR (KBr): 2900, 1640, 1500 cm⁻¹
FD Mass: 690 (M+)

Example 7

(1) To a solution of 1,3,6′-tris-N-benzyloxycarbonyl-3″-N-palmitoylkanamycin A (950 mg) in pyridine was added acetic anhydride (0.96 ml) at ambient temperature. The solution was stirred for 10 minutes and allowed to stand overnight. To the solution was added water (0.2 ml) and the reaction mixture was concentrated under reduced pressure. The resultant residue, dissolved in ethyl acetate (40 ml), was washed successively with water, 1N-hydrochloric acid, saturated aqueous sodium bicarbonate, and saturated aqueous sodium chloride, dried over anhydrous sodium sulfate, and concentrated under reduced pressure to give a residue which was subjected to column chromatography on silica gel (50 g) and eluted with a mixture of chloroform and methanol (50:1 V/V). Fractions containing the object compound were combined and concentrated under reduced pressure to give 2′,3′,4′,2″,4″,6″-hexa-O-acetyl-1,3,6′-tris-N-benzyloxycarbonyl-3″-N-palmitoylkanamycin A (454 mg).

mp: 233°–234° C.
IR (Nujol): 1730, 1680, 1650, 1520, 1230, 1030 cm⁻¹
NMR (CDCl₃, δ): 0.90 (3H, m), 1.27 (28H, s), 1.99–2.15 (18H)

(2) (a) To the solution of potassium hydroxide (215 mg) in methanol (10 ml) was added 2′,3′,4′,2″,4″,6″-hexa-O-acetyl-1,3,6′-tris-N-benzyloxycarbonyl-3″-N-palmitoylkanamycin A (440 mg) and the mixture was stirred at ambient temperature for 40 minutes. The reaction mixture was poured into ice-water (100 ml) and the resultant precipitate was collected by filtration and washed three times with water (20 ml). The precipitate was air-dried to give 1,3,6′-tris-N-benzyloxycarbonyl-3″-N-palmitoylkanamycin A (335 mg).

(b) A solution of 1,3,6′-tris-N-benzyloxycarbonyl-3″-N-palmitoylkanamycin A (335 mg) in a mixture of methanol (10 ml) and conc. hydrochloric acid (0.5 ml) was hydrogenated under atmospheric pressure of hydrogen at ambient temperature for 4 hours in the presence of 10% palladium on carbon (300 mg). The catalyst was filtered off and the filtrate was concentrated under reduced pressure. The resultant residue was suspended in ethanol (20 ml), which was concentrated under reduced pressure to give a residue. This procedure was repeated twice. The residue was dissolved in water (20 ml) and lyophilized to give 3″-N-palmitoylkanamycin A trihydrochloride (145 mg).

mp: >183° C. (dec.)
$[\alpha]_D^{20}$: +58.0° (C1.0, H₂O)
IR (Nujol): 3300–3200, 1620, 1510, 1080, 1030 cm⁻¹
FD Mass: 723 (M+)

Example 8

To a suspension of 1,3,3″-tris-N-tert-butoxycarbonyl-6′-N-palmitoylkanamycin A (500 mg) in anisole (1.5 ml) was added trifluoroacetic acid (5 ml) under ice-cooling. The mixture was stirred for 2 hours at the same temperature and then concentrated in vacuo. The residue was dissolved in water. The solution was concentrated in vacuo. To a solution of the residue was added Domex 1×2 (COH⁻ type, trade mark made by Dom Chemical Co., Ltd.) to adjust pH 10.5. The insolved material was collected by filtration and washed with methanol. The insolved material was suspended in water and adjusted pH 4.5 by trifluoroacetic acid. The insolved material was filtered off and washed with water. The filtrate and washings were combined and lyophilized to give 6′-N-palmitoylkanamycin A trifluoroacetate (230 mg).

mp: 193° C. (dec.)
$[\alpha]_D^{26}$: +57.7° (C=1.22, H₂O)
IR (Nujol): 1670 cm⁻¹
NMR (D₂O,δ): 1.27
FD Mass: 723 (M+)

Example 9

A suspension of 1,6′,3″-tris-N-benzyloxycarbonyl-3-N-palmitoylkanamycin A (800 mg) in a mixture of methanol (30 ml) and 1N-hydrochloric acid (3 ml) was hydrogenated under 1 atmospheric pressure of hydrogen in the presence of palladium black (800 mg) at ambient temperature for six hours. The catalyst was filtered off and washed with water. The filtrate and washings were combined and lyophilized to give 3-N-palmitoylkanamycin A trihydrochloride (580 mg).

mp: 181° C. (dec.)
$[\alpha]_D^{26}$: +62.9° (C=0.12, H₂O)

IR (Nujol): 1620 cm$^{-1}$
NMR (CD$_3$OD, δ): 0.80–1.10 (3H, m), 5.13 (d, J=3 Hz, 1H), 5.37 (d, J=3 Hz, 1H)
FD Mass: 723 (M+)

EXAMPLE 10

(1) A solution of 3,6′,3″-tris-N-benzyloxycarbonyl-1-N-palmitoylkanamycin A (650 mg) in a mixture of dioxane (10 ml), methanol (10 ml) and 1-N-hydrochloric acid (2 ml) was hydrogenated under atmospheric pressure of hydrogen at ambient temperature for 4 hours over 10% palladium on carbon (650 mg). The catalyst was removed by filtration and the filtrate was concentrated under reduced pressure to give a residue. The residue was dissolved in water (40 ml) and filtered off. The filtrate was lyophilized to give 1-N-palmitoylkanamycin A trihydrochloride (417 mg).

mp: >221° C. (dec.)
IR (KBr): 3400–3300, 1640–1630, 1540, 1510, 1140, 1050 cm$^{-1}$
NMR (D$_2$O, δ): 0.91 (3H, m), 1.26 (28H, s)
FD Mass: 723 (M+)

(2) (a) Phosphorus oxychloride (0.29 ml) was added to a mixture of dimethylformamide (0.24 ml) and tetrahydrofuran (0.5 ml) and the suspension was stirred at −5°–0° C. for 10 minutes to the above suspension were added tetrahydrofuran (5 ml) and, next, 3-acetoxytetradecanoic acid (687 mg) at 0°–2° C. with stirring. The mixture was stirred at the same temperature for 30 minutes to prepare an activated acid solution. On the other hand, 3,6′,3″-tris-N-benzyloxycarbonylkanamycin A monotrifluoroacetate (1.2 g) was dissolved in a mixture of tetrahydrofuran (40 ml) and water (10 ml). To the solution was dropwise added the activated acid solution obtained above at 0°–5° C. with stirring, keeping the pH 8 to 9 with triethylamine. The reaction mixture was stirred for 30 minutes at the same temperature. The solution was concentrated under reduced pressure to give a solid. The solid was twice washed with diethylether (20 ml) collected by filtration and air-dried to give a solid. The solid was subjected on a median pressure column chromatography of silica gel (50 g) and eluted with a mixture of chloroform, methanol and conc.ammonia (4:1:0.1 V/V). Fractions containing the object compound were combined and concentrated under reduced pressure to give 3,6′,3″-tris-N-benzyloxycarbonyl-1-N-(3-acetoxy-n-tetradecanoyl)kanamycin A (1.03 g).

(b) To a solution of 3,6′,3″-tris-N-benzyloxycarbonyl-1-N-(3-acetoxy-n-tetradecanoyl)kanamycin A (976 mg) in pyridine (20 ml), acetic anhydride (0.96 ml) was added and stirred at ambient temperature for 30 minutes and kept to stand at ambient temperature for 2 days. The reaction mixture was concentrated under reduced pressure to give a residue. The residue was dissolved in ethyl acetate (60 ml) and the solution was washed with 1N-hydrochloric acid, water, saturated aqueous sodium bicarbonate and saturated aqueous sodium chloride, in turn, dried over anhydrous sodium sulfate, and concentrated under reduced pressure to give a residue. The residue was subjected to a column chromatography on silica gel (60 g) and eluted with a mixture of chloroform and methanol (50:1 V/V). Fractions containing the object compound were collected and concentrated under reduced pressure to give 2′,3′,4′,2″,4″,6″-hexa-O-acetyl-3,6′,3″-tris-N-benzyloxycarbonyl-1-N-(3-acetoxy-n-tetradecanoyl)kanamycin A (864 mg).

mp: 184°–186° C. (melt)
IR (Nujol): 3300, 1730, 1710, 1695, 1645, 1510, 1220, 1030 cm$^{-1}$
NMR (CDCl$_3$, δ): 0.90 (3H, m), 1.27, 1.92–2.10 (18H, m)

(c) A mixture of 2′,3′,4′,2″,4″,6″-hexa-O-acetyl-3,6′,3″-tris-N-benzyloxycarbonyl-1-N-(3-acetoxy-n-tetradecanoyl)kanamycin A (830 mg) in a solution of potassium hydroxide (463 mg) in methanol (17 ml) was stirred at ambient temperature for an hour. The resultant mixture was poured into ice-water (100 ml). Then the resultant precipitate was collected by filtration, washed with water (20 ml) three times, and air-dried to give 3,6′,3″-tris-N-benzyloxycarbonyl-1-N-(3-hydroxy-n-tetradecanoyl)kanamycin A (597 mg).

IR (Nujol): 1680, 1640, 1530, 1290, 1260, 1140, 1040 cm$^{-1}$
NMR (DMSO-d$_6$, δ): 0.90 (3H, m), 1.22 (20H, s), 7.32 (15H, s)

(d) A solution of 3,6′,3″-tris-N-benzyloxycarbonyl-1-N-(3-hydroxy-n-tetradecanoyl)kanamycin A (580 mg) in a mixture of methanol (20 ml) and conc. hydrochloric acid (0.5 ml) was hydrogenated under atmospheric pressure of hydrogen at ambient temperature for 4 hours in the presence of 10% palladium on carbon (0.5 g). The catalyst was removed by filtration and the filtrate was concentrated under reduced pressure to give a residue. The residue was dissolved in water (40 ml) and lyophilized to give 1-N-(3-hydroxy-n-tetradecanoyl)kanamycin A trihydrochloride (349 mg).

mp: >178° C. (dec.)
IR (KBr): 3400–3250, 1630, 1140, 1050 cm$^{-1}$
FD Mass: 711 (M+)

Example 11

A solution of 1-N-(3-acetoxy-n-tetradecanoyl)-3,6′-bis-N-benzyloxycarbonyl-3″-N-trifluoroacetylkanamycin A (0.8 g) in a mixture of tetrahydrofuran (20 ml) and 5N-ammonia hydroxide (5 ml) was stirred at ambient temperature overnight. The solution was poured into ice-water (150 ml). The resultant precipitates were collected by filtration, washed with water, and dried over phosphorus pentoxide under reduced pressure to give 1-N-(3-acetoxy-n-tetradecanoyl)-3,6′-bis-N-benzyloxycarbonylkanamycin A (669 mg).

mp: >263° C. (dec.)
IR (Nujol): 3270, 1685, 1630, 1520, 1260, 1230, 1140, 1050 cm$^{-1}$
NMR (DMSO-d$_6$, δ): 1.95 (3H, s)

Example 12

To a solution of potassium hydroxide (1.05 g) in a mixture of methanol (40 ml) and dimethylsulfoxide (15 ml) was added 1-N-(3-acetoxy-n-tetradecanoyl)-3,6′-bis-N-benzyloxycarbonyl-3″-N-trifluoroacetylkanamycin A (3.5 g) and the mixture was stirred at ambient temperature for one hour. The reaction mixture was poured into ice-water (150 ml). The resultant precipitates were collected by filtration, washed with water until the pH of the washings indicated 7 and air-dried to give 3,6′-bis-N-benzyloxycarbonyl-1-N-(3-hydroxy-n-tetradecanoyl)kanamycin A (2.86 g).

IR (Nujol): 1690, 1640, 1540, 1150, 1050, 1030 cm$^{-1}$
NMR (DMSO-d$_6$, δ): 0.95 (3H, m)

Example 13

(1) To a solution of 3,6′-bis-N-benzyloxycarbonyl-1-N-palmitoyl-3″-N-trifluoroacetylkanamycin A (5 g) in pyridine (100 ml) was added acetic anhydride (5.2 ml) and the mixture was stirred at ambient temperature for 6 hours. An additional acetic anhydride (1 ml) was added with stirring and the resultant mixture was allowed to stand at the same temperature overnight. The reaction mixture was concentrated under reduced pressure to give a residue, which was dissolved in ethyl acetate (200 ml) and washed with aqueous sodium hydrogen carbonate and water and concentrated under reduced pressure. The residue was subjected to column chromatography on silica gel (60 g) and eluted with a mixture of chloroform and methanol (50:1 V/V). Fractions containing the object compound were combined and concentrated under reduced pressure to give 2′,3′,4′,2″,4″,6″-hexa-O-acetyl-3,6′-bis-N-benzyloxycarbonyl-1-N-palmitoyl-3″-N-trifluoroacetylkanamycin A (6.76 g).

NMR (CDCl$_3$, δ): 0.93 (3H, m), 1.28 (28H, s)

(2) To a solution of potassium hydroxide (4 g) in methanol (140 ml), 2′,3′,4′,2″,4″,6″-hexa-O-acetyl-3,6′-bis-N-benzyloxycarbonyl-1-N-palmitoyl-3″-N-trifluoroacetylkanamycin A (6.76 g) was added and the mixture was stirred at ambient temperature for 2 hours. The reaction mixture was poured into ice-water (400 ml). The resultant precipitates were collected by filtration, washed with water until the pH of the washings indicated 7, and dried over phosphorus pentoxide in vacuo to give 3,6′-bis-N-benzyloxycarbonyl-1-N-palmitoylkanamycin A (4.23 g).

IR (Nujol): 3290, 1685, 1640, 1540, 1275, 1230, 1050 cm$^{-1}$

NMR (DMSO-d$_6$, δ): 0.90 (3H, m), 1.63 (28H, s)

Example 14

To a solution of potassium hydroxide (1.16 g) in methanol (40 ml), 2′,3′,4′,2″,4″,6″-hexa-O-acetyl-3″-N-acetyl-1-N-(3-acetoxy-n-tetradecanoyl)-3,6′-bis-N-benzyloxycarbonylkanamycin A (1.9 g) was added and the mixture was stirred at ambient temperature for 3 hours. The resultant suspension was poured into ice-water (200 ml). The resultant precipitates were collected by filtration, washed with water, and air-dried to give 3″-N-acetyl-3,6′-bis-N-benzyloxycarbonyl-1-N-(3-hydroxy-n-tetradecanoyl)kanamycin A (1.20 g) as a solid.

mp: >266° C. (dec.)

IR (Nujol): 3280, 1685, 1640, 1520, 1270, 1230, 1150 cm$^{-1}$

NMR (DMSO-d$_6$, δ): 1.84 (3H, s)

Example 15

Phosphorus oxychloride (0.23 ml) was added to a mixture of dimethylformamide (0.20 ml) and tetrahydrofuran (0.4 ml) and the suspension was stirred at −5°-0° C. for 10 minutes. To the above suspension were added successively tetrahydrofuran (4 ml), and n-pentadecanoic acid (471 mg) at −5°-0° C. with stirring. The mixture was stirred at the same temperature for 30 minutes to prepare an activated acid solution. To a solution of 3,6′-bis-N-benzyloxycarbonyl-3″-N-trifluoroacetylkanamycin A (1.5 g) in a mixture of tetrahydrofuran (40 ml) and water (12 ml) was dropwise added the activated acid solution obtained above keeping the pH between 8 and 9 with triethylamine. The resultant mixture was stirred for 30 minutes at the same temperature and concentrated under reduced pressure. The resultant solid was collected by filtration, washed in turn with 1N-hydrochloric acid (20 ml), a mixture of iso-propyl alcohol (30 ml) and diethyl ether (30 ml), water, and diethyl ether and air-dried to give 3,6-bis-N-benzyloxycarbonyl-1-N-n-pentadecanoyl-3″-N-trifluoroacetylkanamycin A (1.59 g).

mp: >284° C. (dec.)

IR (Nujol): 3290, 1690, 1640, 1530, 1260, 1210, 1180, 1050 cm$^{-1}$

NMR (DMSO-d$_6$, δ): 0.93 (3H, m), 1.07 (26H, s)

Example 16

The following compounds were obtained according to a similar manner to that of Example 15.

(1) 3,6′-Bis-N-benzyloxycarbonyl-1,3″-bis-N-n-octanoylkanamycin A.

IR (Nujol): 1690, 1640, 1540 cm$^{-1}$ (2) 3,6′-Bis-N-benzyloxycarbonyl-1-N-(2-hexyl-n-decanoyl)-3″-N-trifluoroacetylkanamycin A.

mp: >276° C. (dec.)

IR (Nujol): 3280, 1690, 1640, 1530, 1270, 1175, 1050 cm$^{-1}$

NMR (DMSO-d$_6$, δ): 1.20 (24H, s)

(3) 1-N-(3-Acetoxy-n-tetradecanoyl)-3,6′-bis-N-benzyloxycarbonyl-3″-N-trifluoroacetylkanamycin A.

mp: >188° C. (dec.)

IR (Nujol): 3270, 1685, 1630, 1530, 1160, 1040 cm$^{-1}$

NMR (DMSO-d$_6$, δ): 0.90 (3H, m), 1.92 (3H, s)

(4) 3,6′-Bis-N-benzyloxycarbonyl-1-N-n-tridecyloxyacetyl-3″-N-trifluoroacetylkanamycin A.

mp: 240° C. (dec.)

IR (Nujol): 1690, 1540 cm$^{-1}$

NMR (DMSO-d$_6$, δ): 0.83-1.00 (3H, m), 7.30 (10H, s)

(5) 1-N-(3-Acetoxy-n-tetradecanoyl)-3,6′-bis-N-benzyloxycarbonyl-3″-N-[N-(benzyloxycarbonyl)-glycyl]-kanamycin A.

mp: >256° C. (dec.)

IR (Nujol): 1690, 1530, 1260, 1230, 1140, 1040 cm$^{-1}$

NMR (DMSO-d$_6$, δ): 0.88 (3H, m), 1.92 (3H, s)

(6) 3-6′-Bis-N-benzyloxycarbonyl-1-N-(Z)-13-docosenoyl-3″-N-trifluoroacetylkanamycin A.

mp: >251° C. (dec.)

IR (Nujol): 3290, 1690, 1640, 1540, 1170, 1050 cm$^{-1}$

NMR (DMSO-d$_6$, δ): 0.90 (3H, m)

(7) 3,6′,3″-Tris-N-benzyloxycarbonyl-1-N-palmitoylkanamycin A.

mp: >276° C. (dec.)

IR (Nujol): 3280–3260, 1680, 1630, 1530, 1290, 1145, 1040 cm$^{-1}$

NMR (DMSO-d$_6$, δ): 0.90 (3H, m), 1.26 (28H, s)

(8) 3,6′-Bis-N-benzyloxycarbonyl-1-N-n-hexadecyloxycarbonyl-3″-N-trifluoroacetylkanamycin A.

mp: >268° C.

IR (Nujol): 3300, 1700, 1680, 1215, 1180, 1040 cm$^{-1}$

NMR (DMSO-d$_6$, δ): 0.92 (3H, m)

(9) 3,6′-Bis-N-tert-butoxycarbonyl-1-N-n-hexadecylthiocarbonyl-3″-N-trifluoroacetylkanamycin A.

mp: >226° C. (dec.)

IR (Nujol): 3280, 1700, 1680, 1635, 1530, 1165, 1080 cm$^{-1}$

NMR (DMSO-d$_6$, δ): 0.90 (3H, m)

(10) 3,6′-Bis-N-benzyloxycarbonyl-1-N-n-pentadecylaminocarbonyl-3″-N-trifluoroacetylkanamycin A.

mp: >236° C. (dec.)

IR (Nujol): 3300, 1690, 1620, 1540, 1280, 1160, 1040 cm$^{-1}$

NMR (DMSO-d$_6$, δ): 0.90 (3H, m)

Example 17

(1) To a solution of 3″-N-acetyl-3,6′-bis-N-benzyloxycarbonyl-1-N-palmitoylkanamycin A (1.96 g) in absolute pyridine (40 ml) was added acetic anhydride (2.26 ml) and the mixture was stirred at ambient temperature for one hour and allowed to stand at the same temperature overnight. To the reaction mixture was added water (1 ml) at ambient temperature and concentrated under reduced pressure. The resultant residue, dissolved in ethyl acetate (80 ml), was washed, in turn with 1N hydrochloric acid, aqueous sodium chloride, aqueous sodium bicarbonate, and aqueous sodium chloride and dried over anhydrous sodium sulfate. The solvent was removed by evaporation under reduced pressure to give a residue, which was subjected to column chromatography on silica gel (60 g) and eluted with a mixture of chloroform and methanol (50:1 V/V). Fractions containing the object compound were combined and concentrated under reduced pressure to give 3″-N-acetyl-2′,3′,4′,2″,4″,6″-hexa-O-acetyl-3,6′-bis-N-benzyloxycarbonyl-1-N-palmitoylkanamycin A (2.14 g)
mp: 222°–223° C.
$[\alpha]_D^{20}$: 75.3° (C1.0, CHCl$_3$)
IR (Nujol): 3300, 1740, 1650, 1530, 1230, 1040 cm$^{-1}$
NMR (CDCl$_3$, δ): 0.95 (3H, m), 1.20 (28H, s), 1.90 (3H, s), 2.00–2.20 (18H, m)

(2) To a solution of potassium hydroxide (920 mg) in methanol (40 ml) was added 3″-N-acetyl-2′,3′,4′,2″,4″,6″-hexa-O-acetyl-3,6′-bis-N-benzyloxycarbonyl-1-N-palmitoylkanamycin A (2.1 g). The mixture was stirred at ambient temperature for one hour. The reaction mixture was poured into ice-water (150 ml). The resultant precipitate was collected by filtration and the filtrate was washed with water until the pH of the washings indicated 7 and air-dried to give 3″-N-acetyl-3,6′-bis-N-benzyloxycarbonyl-1-N-palmitoylkanamycin A (1.53 g).
IR (Nujol): 1680, 1640, 1520, 1270, 1230, 1150 cm$^{-1}$

Example 18

(a) A solution of 3,6′-bis-N-benzyloxycarbonyl-3″-N-[N-(benzyloxycarbonyl)glycyl]-1-N-tert-butoxycarbonylkanamycin A (0.92 g) in a mixture of trifluoroacetic acid (10 ml) and anisole (3 ml) was stirred under ice-cooling for one hour. The solution was concentrated under reduced pressure to give 3,6′-bis-N-benzyloxycarbonyl-3″-N-[N-(benzyloxycarbonyl)glycyl]kanamycin A.

(b) To a solution of the resultant residue including 3,6′-bis-N-benzyloxycarbonyl-3″-N-[N-(benzyloxycarbonyl)glycyl]kanamycin A in a mixture of tetrahydrofuran (40 ml) and water (10 ml), was dropwise added a solution of palmitoyl chloride (254 mg) in tetrahydrofuran (10 ml) at 0°–5° C. with stirring, keeping the pH 8–9 with triethylamine. The mixture was stirred at the same temperature for one hour and the reaction mixture was concentrated under reduced pressure to give a solid, which was collected by filtration and washed twice with 1N-hydrochloric acid 20 ml, isopropyl alcohol (20 ml), diethyl ether (20 ml), water until the pH of the washings indicated 7, and a mixture of isopropyl alcohol (10 ml) and diethyl ether (10 ml), in turn, and air-dried to give 3,6′-bis-N-benzyloxycarbonyl-3″-N-[N-(benzyloxycarbonyl)glycyl]-1-N-palmitoylkanamycin A (910 mg) as a solid.
mp: >269° C. (dec.)
IR (Nujol): 3280, 1690, 1650, 1540, 1270, 1150, 1050 cm$^{-1}$
NMR (DMSO-d$_6$, δ): 0.90 (3H, m), 1.22 (28H, s)

Example 19

The following compounds were obtained according to a similar manner to that of Example 18.

(1) 3″-N-Acetyl-3,6′-bis-N-benzyloxycarbonyl-1-N-palmitoylkanamycin A.
NMR (DMSO-d$_6$, δ): 0.85 (3H, m), 1.83 (3H, s)

(2) 3″-Benzyloxyacetyl-3,6′-bis-N-benzyloxycarbonyl-1-N-palmitoylkanamycin A.
IR (Nujol): 1690, 1640, 1540 cm$^{-1}$
NMR (DMSO-d$_6$, δ): 1.20 (s), 4.57 (s), 7.27 (s), 7.30 (s), 7.33 (s)

(3) 1-N-(3-Acetoxy tetradecanoyl)-3,6′-bis-N-benzyloxycarbonyl-3″-N-[N-(benzyloxycarbonyl)glycyl]kanamycin A.
mp: >256° C. (dec.)
IR (Nujol): 1690, 1530, 1260, 1230, 1140, 1040 cm$^{-1}$
NMR (DMSO-d$_6$, δ): 0.88 (3H, m), 1.92 (3H, s)

Example 20

(1) To a solution of 1,3,6′-tris-N-benzyloxycarbonylkanamycin A (700 mg) in a mixture of tetrahydrofuran (40 ml) and water (10 ml), was dropwise added palmitoyl chloride (0.26 g) under ice-cooling, keeping the pH between 8 and 8.5 with triethylamine. The mixture was stirred at the same temperature for one hour. The solution was concentrated under reduced pressure to give a solid, which was washed twice with diethyl ether (50 ml) and water (50 ml), collected by filtration, and air-dried to give 1,3,6′-tris-N-benzyloxycarbonyl-3″-N-palmitoylkanamycin A (950 mg).
mp: >288° C. (dec.)
IR (Nujol): 3300, 1685, 1650, 1535, 1520, 1230, 1150, 1040 cm$^{-1}$
NMR (DMSO-d$_6$, δ): 0.87 (3H, m), 1.22 (24H, s), 7.25 (15H, s)

(2) To a solution of 3,6′-bis-N-benzyloxycarbonyl-1-N-tert-butoxycarbonylkanamycin A (3 g) in dimethylsulfoxide (25 ml) was added N-palmitoyloxysuccinimide (1.37 g) at ambient temperature. The mixture was stirred at the same temperature overnight. The mixture was poured into water (150 ml) to give a precipitate. The precipitate was collected by filtration, washed with water and diethyl ether in turn, and dried over phosphorus pentoxide in vacuo to give 3,6′-bis-N-benzyloxycarbonyl-1-N-tert-butoxycarbonyl-3″-N-palmitoylkanamycin A (3.50 g).
IR (Nujol): 1690, 1520 cm$^{-1}$

Example 21

To a solution of 1,6′,3″-tris-N-benzyloxycarbonylkanamycin A (283 mg) in a mixture of tetrahydrofuran (20 ml) and water (5 ml) was added palmitoyl chloride (88 mg) under ice-cooling, keeping the pH between 8 and 9 with triethylamine. The mixture was stirred under the same condition for 2 hours. Tetrahydrofuran was removed from the reaction mixture by evaporation to give a precipitate suspended in water. The precipitate was collected, washed with water, and dried over phosphorus pentoxide in vacuo to give 1,6′,3″-tris-N-benzyloxycarbonyl-3-N-palmitoylkanamycin A (310 mg).
mp: 292° C. (dec.)
IR (Nujol): 1680, 1530 cm$^{-1}$
NMR (DMSO-d$_6$, δ): 1.33 (s, 28H), 7.33 (s, 15H)

Example 22

(a) To a suspension of 1,6′-bis-N-benzyloxycarbonyl-3-N-tert-butoxycarbonyl-3″-N-trifluoroacetylkanamycin A (800 mg) in anisole (2.4 ml) was added trifluoroacetic acid (8 ml) under ice-cooling. The mixture was stirred for 2 hours at the same temperature and concentrated in vacuo to give 1,6′-bis-N-benzyloxycarbonyl-3″-N-trifluoroacetylkanamycin A.

(b) To a solution of the residue including 1,6'-bis-N-benzyloxycarbonyl-3''-N-trifluoroacetylkanamycin A a mixture of tetrahydrofuran (40 ml) and water (10 ml) was added palmitoyl chloride (254 mg) under ice-cooling, keeping the pH between 8 and 9 with triethylamine. The mixture was stirred for one hour under the same condition. Tetrahydrofuran was removed from the mixture by evaporation to give a precipitate, which was collected, washed with 1N-hydrochloric acid, water and diethyl ether in turn, and dried over phosphorus pentoxide in vacuo to give 1,6'-bis-N-benzyloxycarbonyl-3-N-palmitoyl-3''-N-trifluoroacetylkanamycin A (850 mg).

IR (Nujol): 1700, 1530 cm$^{-1}$
NMR (DMSO-d$_6$, $\delta$): 0.87–1.03 (3H, m), 7.33 (10H, s)

Example 23

(a) A mixture of 6'-N-benzyloxycarbonyl-1,3,3''-tris-N-tert-butoxycarbonylkanamycin A (500 mg) in a mixture of N,N-dimethylformamide (10 ml), tetrahydrofuran (5 ml) and methanol (5 ml) was hydrogenated in 1 atmospheric pressure of hydrogen in the pressure of palladium black (500 mg) at ambient temperature for 4 hours. 1N-hydrochloric acid (0.6 ml) was added to the mixture. The mixture was further hydrogenated overnight. The catalyst was filtered off and washed with N,N-dimethylformamide. The filtrate and washings were combined and concentrated in vacuo to give 1,3,3''-tris-N-tert-butoxycarbonylkanamycin A.

(b) To a solution of the residue including 1,3,3''-tris-N-tert-butoxycarbonylkanamycin A in a mixture of tetrahydrofuran (50 ml) and water (10 ml) was added palmitoyl chloride (150 mg) under ice-cooling, keeping the pH between 8 and 9 with triethylamine. The mixture was stirred under the same condition for one hour. Tetrahydrofuran was removed from the reaction mixture by evaporation in vacuo to give a solid. The solid was washed with water and dried over phosphorus pentoxide in vacuo to give 1,3,3''-tris-N-tert-butoxycarbonyl-6'-N-palmitoylkanamycin A (518 mg).

mp: 238° C. (dec.)
IR (Nujol): 1690, 1520 cm$^{-1}$
NMR (DMSO-d$_6$, $\delta$): 1.23, 1.39

Example 24

(a) To a suspension of 3,6'-bis-N-benzyloxycarbonyl-1-N-tert-butoxycarbonyl-3''-N-palmitoylkanamycin A (1 g) in anisole (3 ml) was added trifluoroacetic acid (10 ml) under ice-cooling. The reaction mixture was stirred at the same temperature for 2 hours. The reaction mixture was concentrated in vacuo to give 3,6'-bis-N-benzyloxycarbonyl-3''-N-palmitoylkanamycin A.

(b) To a solution of the residue including 3,6'-bis-N-benzyloxycarbonyl-3''-N-palmitoylkanamycin A in a mixture of methanol (10 ml), N,N-dimethylformamide (5 ml), and dimethylsulfoxide (8 ml) were added ethyl trifluoroacetate (2.84 g) and triethylamine (2.8 ml) at ambient temperature. The mixture was stirred for 11 days. Removal of the methanol and pouring the resulting residue into water (80 ml) gave a precipitate, which was collected, washed with water and diethyl ether in turn, and dried over phosphorus pentoxide in vacuo to afford 3,6'-bis-N-benzyloxycarbonyl-3''-N-palmitoyl-1-N-trifluoroacetylkanamycin A (683 mg).

IR (Nujol): 1690, 1540 cm$^{-1}$
NMR (DMSO-d$_6$, $\delta$): 0.77–1.03 (3H, m), 7.33 (10H, s)

Example 25

The following compound was obtained according to a similar manner to that of Example 24.

1-N-Acetyl-3,6'-bis-N-benzyloxycarbonyl-3''-N-palmitoylkanamycin A.
IR (Nujol): 1680, 1630, 1530 cm$^{-1}$
NMR (DMSO-d$_6$, $\delta$): 0.87 (m), 1.27, 1.77 (s), 7.30 (s)

Example 26

To a solution of 3,6'-bis-N-benzyloxycarbonyl-1-N-palmitoylkanamycin A (500 mg) in a mixture of tetrahydrofuran (30 ml) and water (8 ml), a solution of acryloyl chloride (468 mg) in tetrahydrofuran (5 ml) was dropwise added with stirring under ice-cooling, keeping the pH 8 to 9 with triethylamine. The mixture was stirred at ambient temperature for an hour. The reaction mixture was concentrated under reduced pressure to give a solid. The solid was collected by filtration, washed with 1N-hydrochloric acid (30 ml), diethyl ether (60 ml), water, and diethyl ether, in turn, and air-dried to give 3''-N-acryloyl-3,6'-bis-N-benzyloxycarbonyl-1-N-palmitoylkanamycin A (624 mg).

mp: >257° C. (dec.)
IR (Nujol): 3300, 1690, 1640, 1540, 1270, 1150, 1040 cm$^{-1}$
NMR (DMSO-d$_6$, $\delta$): 0.90 (3H, m), 1.23 (28H, s)

Example 27

The following compounds were obtained according to a similar manner to that of Example 26.

(1) 3,6'-Bis-N-benzyloxycarbonyl-3''-N-(3-carboxypropionyl)-1-N-palmitoylkanamycin A.
mp: >252° C. (dec.)
IR (Nujol): 3300, 1690, 1640, 1530, 1270, 1150, 1040 cm$^{-1}$ (2) 3,6'-Bis-N-benzyloxycarbonyl-1-N-(3-hydroxytetradecanoyl)-3''-N-trifluoroacetylkanamycin A.
mp: >265° C. (dec.)
IR (Nujol): 1690, 1640, 1540, 1270, 1210, 1160 cm$^{-1}$
NMR (DMSO-d$_6$, $\delta$): 0.88 (3H, m), 1.22 (28H, s)

(3) 3''-N-benzoyl-3,6'-bis-N-benzyloxycarbonyl-1-N-palmitoylkanamycin A.
mp: >284° C. (dec.)
IR (Nujol): 3280, 1710, 1680, 1620, 1540, 1300, 1260, 1240, 1080, 1040 cm$^{-1}$
NMR (DMSO-d$_6$, $\delta$): 0.90 (3H, m), 1.20 (28H, s)

Example 28

To a solution of 3,2',6'-tris-N-benzyloxycarbonyl-3',4'-dideoxy-3''-N-trifluoroacetylkanamycin B (300 mg) in a mixture of tetrahydrofuran (20 ml) and water (7 ml) was added palmitoyl chloride (92 mg) under ice-cooling, keeping the pH between 8 and 9. The mixture was stirred for 30 minutes under the same condition. From the mixture, tetrahydrofuran was removed by evaporation. To the resultant mixture was added water to give a precipitate. The precipitate was filtered off and washed with water. The precipitate was dissolved in N,N-dimethylformamide (2 ml) and the solution was dried with magnesium sulfate. The insolved material and removed by filtration and to the filtrate was added silica gel (600 mg). The mixture was concentrated in vacuo to dryness. The mixture was subjected to column chromatography on silica gel and eluted with methanol-chloroform (1:25, 1:10, and 1:4 in turn). The fractions, containing the desired compound, were combined and concentrated in vacuo to give 3,2',6'-tris-N-benzyloxycarbonyl-3',4'-dideoxy-1-N-palmitoyl-3''-N-trifluoroacetylkanamycin B (176 mg).

IR (Nujol): 1680, 1520 cm$^{-1}$

Example 29

A mixture of 3,2',6'-tris-N-benzyloxycarbonyl-3''-N-trifluoroacetylkanamycin B (500 mg) and N-palmitoyloxysuccinimide (189 mg) in N,N-dimethylformamide (10 ml) was stirred at ambient temperature for 18 days. The reaction mixture was poured into water (50 ml). The resulting precipitate was collected, washed with water and diethylether in turn, and dried over phosphorus pentoxide in vacuo to give 3,2',6'-tris-N-benzyloxy-carbonyl-1-N-palmitoyl-3''-N-trifluoroacetylkanamycin B (536 mg).

NMR (DMSO-d$_6$, δ): 0.84 (3H, t, J=6 Hz)

Example 30

The following compound was obtained according to a similar manner to that of Example 29.

3,2',6',3''-tetrakis-N-benzyloxycarbonyl-3',4'-dideoxy-1-N-palmitoylkanamycin B.

IR (Nujol): 1680, 1540 cm$^{-1}$

Example 31

The following compounds were obtained according to a similar manner to that of Example 15.

(1) 3,6'-Bis-N-benzyloxycarbonyl-1-N-n-octanoyl-3''-N-trifluoroacetylkanamycin A.

mp; >297° C. (dec.).

IR (Nujol): 3270, 1690, 1640, 1530, 1160, 1040 cm$^{-1}$

NMR (DMSO-d$_6$, δ): 0.90 (3H, m), 1.23 (12H, s)

(2) 3,6'-Bis-N-benzyloxycarbonyl-1-N-n-decanoyl-3''-N-trifluoroacetylkanamycin A as a solid.

mp; >285° C.

IR (Nujol): 1690, 1640, 1540, 1265, 1160, 1040 cm$^{-1}$

NMR (DMSO-d$_6$, δ): 0.90 (3H, m), 1.23 (16H, s)

(3) 3,6'-Bis-N-benzyloxycarbonyl-1-N-lauroyl-3''-N-trifluoroacetylkanamycin A.

mp; >278° C. (dec.).

IR (Nujol): 3260, 1680, 1630, 1530, 1260, 1160, 1040 cm$^{-1}$ (4) 3,6'-Bis-N-benzyloxycarbonyl-1-N-myristoyl-3''-N-trifluoroacetylkanamycin A.

mp; >273° C. (dec.).

IR (Nujol): 1690, 1640, 1540, 1260, 1180, 1050 cm$^{-1}$

NMR (DMSO-d$_6$, δ): 0.90 (3H, m)

(5) 3,6'-Bis-N-benzyloxycarbonyl-1-N-palmitoyl-3''-N-trifluoroacetylkanamycin A.

IR (Nujol): 1690–1680, 1530, 1040–1010 cm$^{-1}$ (6) 3,6'-Bis-N-benzyloxycarbonyl-1-N-n-heptadecanoyl-3''-N-trifluoroacetylkanamycin A.

mp; >285° C. (dec.).

IR (Nujol): 3260, 1680, 1630, 1520, 1170, 1070, 1050 cm$^{-1}$

NMR (DMSO-d$_6$, δ): 0.93 (3H, m)

(7) 3,6'-Bis-N-benzyloxycarbonyl-1-N-stearoyl-3''-N-trifluoroacetylkanamycin A.

mp; >264° C. (dec.).

IR (Nujol): 1680, 1630, 1530, 1160, 1070, 1035 cm$^{-1}$

NMR (DMSO-d$_6$, δ): 0.92 (3H, m), 1.24 (32H, s)

(8) 3,6'-Bis-N-benzyloxycarbonyl-1-N-n-icosanoyl-3''-N-trifluoroacetylkanamycin A.

mp. >288° C. (dec.).

IR (Nujol): 3270, 1680, 1630, 1530, 1170, 1070, 1040 cm$^{-1}$

NMR (DMSO-d$_6$, δ): 0.90 (3H, m), 1.25 (36H, s)

Example 32

The following compounds were obtained according to a similar manner to that of Example 1.

(1) 1-N-n-Octanoyl-3''-N-trifluoroacetylkanamycin A dihydrochloride, mp; >193° C. (dec.).

IR (Nujol): 1705, 1625, 1160, 1030 cm$^{-1}$

NMR (CD$_3$OD, δ): 5.12 (1H, d, J=4 Hz)

FD Mass: 707 (M+)

(2) 1-N-n-Decanoyl-3''-N-trifluoroacetylkanamycin A dihydrochloride.

mp; >210° C. (dec.).

IR (Nujol): 1700, 1620, 1160, 1020 cm$^{-1}$

NMR (D$_2$O, δ): 0.90 (3H, m)

FD Mass: 735 (M+)

(3) 1-N-Lauroyl-3''-N-trifluoroacetylkanamycin A dihydrochloride.

mp. >183° C. (dec.).

IR (Nujol): 1700, 1640–1620, 1560–1540, 1160, 1010 cm$^{-1}$

FD Mass: 763 (M+)

(4) 1-N-Myristoyl-3''-N-trifluoroacetylkanamycin A dihydrochloride.

mp. >194° C.

IR (Nujol): 1700, 1630, 1160, 1030 cm$^{-1}$

NMR (D$_2$O, δ): 0.90 (3H, m)

FD Mass: 791 (M+)

(5) 1-N-Palmitoyl-3''-N-trifluoroacetylkanamycin A dihydrochloride.

mp. 230° C. (dec.).

$[α]_D^{26}$: +67.8° (C1.09, H$_2$O)

IR (Nujol): 3250, 1705, 1640–30, 1550, 1210, 1180, 1160, 1080, 1050–1030 cm$^{-1}$ NMR (CD$_3$OD, δ): 0.88 (3H, t, J=6 Hz), 5.11 (1H, d, J=3 Hz), 5.48 (1H, d, J=3 Hz)

FD Mass: 819 (M+), 723 (M+ −96), 658 (M+ −161), 562 (M+ −257)

(6) 1-N-n-Heptadecanoyl-3''-N-trifluoroacetylkanamycin A dihydrochloride.

mp. >225° C. (dec.).

IR (Nujol): 1700, 1630, 1550, 1160, 1030 cm$^{-1}$

NMR (CD$_3$OD, δ): 5.07 (1H, d, J=4 Hz), 5.43 (1H, d, J=3 Hz)

FD Mass: 833 (M+ +1)

(7) 1-N-Stearoyl-3''-N-trifluoroacetylkanamycin A dihydrochloride.

mp. >233° C. (dec.).

$[α]_D^{20}$: +52.9° (C2.0, H$_2$O)

IR (Nujol): 3300, 1700, 1630, 1550, 1160, 1035 cm$^{-1}$

NMR (D$_2$O, δ): 1.26 (s)

FD Mass: 847 (M+)

(8) 1-N-n-Icosanoyl-3''-N-trifluoroacetylkanamycin A dihydrochloride.

mp. >223° C. (dec.).

IR (Nujol): 3300, 1700, 1630, 1540, 1160, 1080, 1030 cm$^{-1}$

NMR (CD$_3$OD, δ): 0.95 (3H, m), 5.10 (1H, d, J=4 Hz), 5.46 (1H, d, J=3,5 Hz) FD Mass: 875 (M+)

Example 33

A solution of 2',3',4',2'',4''-penta-O-acetyl-3,6'-bis-N-benzyloxycarbonyl-6''-O-(diphenyl phosphoryl)-1-N-palmitoyl-3''-N-trifluoroacetylkanamycin A (855 mg) in a mixture of methanol (40 ml) and 28% concentrated ammonia (15 ml) was stirred at 60° C. for 7.5 hours. The reaction mixture was concentrated under reduced pressure to give a residue. To a solution of the residue in dimethylsulfoxide (20 ml) were added triethylamine (0.2 ml) and ethyl trifluoroacetate (0.5 ml) at ambient temperature and the mixture was stirred at the same temperature for an hour. The reaction mixture was poured into diethylether (200 ml). The resultant precipitates were collected by filtration and washed twice with diethylether (30 ml) and air-dried to give 3,6'-bis-N-benzyloxycarbonyl-6''-O-phosphono-1-N-palmitoyl-3''-N-trifluoroacetylkanamycin A (318 mg).
IR (Nujol): 1700, 1685, 1640, 1540, 1275, 1085 cm$^{-1}$
NMR (DMSO-d$_6$, δ): 0.90 (3H, m), 7.32 (10H, s)

Example 34

The following compounds were obtained according to a similar manner to that of Example 26.
(1) 3,6'-Bis-N-benzyloxycarbonyl-3''-N-(N-benzyloxycarbonylglycyl)-1-N-n-pentadecanoylkanamycin A.
mp; >217° C. (dec.).
IR (Nujol): 3300, 1690, 1535, 1270, 1150, 1050 cm$^{-1}$
NMR (DMSO-d$_6$, δ): 0.92 (3H, m).
(2) 3,6'-Bis-N-benzyloxycarbonyl-3''-N-[(R,S)-3-hydroxybutyryl]-1-N-palmitoylkanamycin A.
mp; >205° C. (dec.).
IR (Nujol): 3380, 1720 (sh), 1690, 1640, 1540, 1270, 1150, 1045 cm$^{-1}$
NMR (DMSO-d$_6$, δ): 0.90 (3H, m)
(3) 3,6'-Bis-N-benzyloxycarbonyl-3''-N-[(R,S)-2-hydroxypropionyl]-1-N-palmitoylkanamycin A.
IR (Nujol): 1720, 1680, 1640, 1530, 1280, 1040 cm$^{-1}$
NMR (DMSO-d$_6$, δ): 0.90 (3H, m)
(4) 3,6'-Bis-N-benzyloxycarbonyl-3''-N-[(D,L)-2,4-bis-(benzyloxycarbonylamino)butyryl]-1-N-palmitoylkanamycin A.
mp; >230° C. (dec.).
IR (Nujol): 3280, 1690, 1640, 1300, 1225, 1150, 1010 cm$^{-1}$
NMR (DMSO-d$_6$, δ): 0.90 (3H, m)

Example 35

The following compounds were obtained according to a similar manner to that of Example 15.
(1) 3,6'-Bis-N-benzyloxycarbonyl-3''-N-(N-benzyloxycarbonylglycyl)-1-N-n-pentadecylaminocarbonylkanamycin A.
IR (Nujol): 3300, 1690, 1540, 1270, 1155, 1045 cm$^{-1}$
NMR (DMSO-d$_6$, δ): 0.91 (3H, m)
(2) 3,6'-Bis-N-benzyloxycarbonyl-3''-N-(N-benzyloxycarbonylglycyl)-1-N-n-hexadecyloxycarbonylkanamycin A.
mp; >246° C. (dec.).
IR (Nujol): 3200, 1690, 1540, 1270, 1150, 1045 cm$^{-1}$
NMR (DMSO-d$_6$, δ): 0.90 (3H, m)
(3) 3,6'-Bis-N-benzyloxycarbonyl-1-N-n-tridecyloxycarbonyl-3''-N-trifluoroacetylkanamycin A.
mp; >268° C. (dec.).
IR (Nujol): 3280, 1680, 1530, 1220, 1160, 1040 cm$^{-1}$
NMR (DMSO-d$_6$, δ): 0.90 (3H, m)
(4) 3,6'-Bis-N-benzyloxycarbonyl-1-N-n-tetradecyloxycarbonyl-3''-N-trifluoroacetylkanamycin A.
mp; >263° C. (dec.).
IR (Nujol): 3300, 1700, 1685, 1535, 1280, 1165, 1040 cm$^{-1}$
NMR (DMSO-d$_6$, δ): 0.90 (3H, m)
(5) 3,6'-Bis-N-benzyloxycarbonyl-1-N-n-pentadecyloxycarbonyl-3''-N-trifluoroacetylkanamycin A.
mp; >263° C. (dec.).
IR (Nujol): 3300, 1700, 1540, 1290, 1170, 1045 cm$^{-1}$
NMR (DMSO-d$_6$, δ): 0.90 (3H, m)
(6) 3,6'-Bis-N-benzyloxycarbonyl-1-N-n-heptadecyloxycarbonyl-3''-N-n-trifluoroacetylkanamycin A.
mp; >277° C. (dec.).
IR (Nujol): 3280, 1700, 1690, 1530, 1220, 1160, 1040 cm$^{-1}$
NMR (DMSO-d$_6$, δ): 0.91 (3H, m)
(7) 3,6'-Bis-N-benzyloxycarbonyl-1-N-n-octadecyloxycarbonyl-3''-N-trifluoroacetylkanamycin A.
IR (Nujol): 3330, 1690, 1545, 1170, 1045 cm$^{-1}$
NMR (DMSO-d$_6$, δ): 0.92 (3H, m)
(8) 3,6'-Bis-N-benzyloxycarbonyl-1-N-n-nonadecyloxycarbonyl-3''-N-trifluoroacetylkanamycin A.
IR (Nujol): 3300, 1750, 1690, 1530, 1285, 1220, 1165, 1040 cm$^{-1}$
NMR (DMSO-d$_6$, δ): 0.90 (3H, m)
(9) 3,6'-Bis-N-benzyloxycarbonyl-3''-N-trifluoroacetyl-1-N-(3,7,11-trimethyldodecyloxycarbonyl)kanamycin A.
IR (Nujol): 3320, 1700 (sh), 1695, 1545, 1160, 1075, 1045 cm$^{-1}$
NMR (DMSO-d$_6$, δ): 0.90 (12H, broad d, J=6 Hz)
(10) 3,6'-Bis-N-benzyloxycarbonyl-1-N-(1-methyltridecyloxycarbonyl)-3''-N-trifluoroacetylkanamycin A.
mp; >272° C. (dec.).
IR (Nujol): 3300, 1700, 1530, 1260, 1220, 1160, 1040 cm$^{-1}$
NMR (DMSO-d$_6$, δ): 0.93 (3H, m)
(11) 3,6'-Bis-N-benzyloxycarbonyl-3''-N-(N-benzyloxycarbonylglycyl)-1-N-[(R,S)-3-dodecanoyloxytetradecanoyl]kanamycin A.
mp; >234° C. (dec.).
IR (Nujol): 3300, 1690, 1540, 1270, 1150, 1040 cm$^{-1}$
NMR (DMSO-d$_6$, δ): 0.92 (3H, m)
(12) 1-N-[(R,S)-3-acetoxyoctadecanoyl]-3,6'-bis-N-benzyloxycarbonyl-3''-N-trifluoroacetylkanamycin A.
mp; >272° C. (dec.).
IR (Nujol): 3300, 1690, 1540, 1170, 1040 cm$^{-1}$
NMR (DMSO-d$_6$, δ): 0.90 (3H, m), 1.90 (3H, s)
(13) 1-N-[(R,S)-3-Acetoxydecanoyl]-3,6'-bis-N-benzyloxycarbonyl-3''-N-trifluoroacetylkanamycin A.
IR (Nujol): 3300, 1705, 1540, 1055 cm$^{-1}$
NMR (DMSO-d$_6$, δ): 0.90 (3H, m), 1.93 (3H, s)
(14) 1-N-[(R,S)-3-Acetoxyhexadecanoyl]-3,6'-bis-N-benzyloxycarbonyl-3''-N-trifluoroacetylkanamycin A.
NMR (DMSO-d$_6$, δ): 0.91 (3H, m), 1.95 (3H, s)

Example 36

The following compounds were obtained according to a similar manner to that of Example 1.
(1) 1-N-Palmitoyl-6''-O-phosphono-3''-N-trifluoroacetylkanamycin A.
mp; >164° C. (dec.).
[α]$_D^{20}$; +27.3° (C1.0, H$_2$O)
IR (Nujol): 1710, 1635, 1550, 1210, 1180, 1155, 1030 cm$^{-1}$
NMR (CD$_3$OD, δ): 0.93 (3H, m)
(2) 3''-N-Glycyl-1-N-n-pentadecylaminocarbonylkanamycin A trihydrochloride.
mp; >169° C. (dec.).
IR (Nujol): 3250, 1680, 1560, 1260, 1140, 1030 cm$^{-1}$
NMR (CD$_3$OD, δ): 0.96 (3H, m)
(3) 3''-N-Glycyl-1-N-n-pentadecanoylkanamycin A trihydrochloride.
mp; >97° C. (dec.).
IR (Nujol): 1670, 1300, 1140, 1080, 1030 cm$^{-1}$
NMR (CD$_3$OD, δ): 0.93 (3H, m), 5.23 (1H, d, J=4 Hz) 5.55 (1H, d, J=3 Hz)
FD Mass: 766 (M$^+$), 788 (M$^+$+Na)
(4) 1-N-n-Hexadecyloxycarbonyl-3''-N-glycylkanamycin A trihydrochloride.
mp; >197° C. (dec.).

IR (Nujol): 3300, 1690, 1540, 1260, 1140, 1035 cm$^{-1}$
NMR (CD$_3$OD, δ): 0.95 (3H, m).

(5) 3''-N-[(R,S)-3-Hydroxybutyryl]-1-N-palmitoylkanamycin A dihydrochloride.
mp; >121° C. (dec.).
IR (Nujol): 3230, 1720, 1630, 1240, 1030 cm$^{-1}$
NMR (CD$_3$OD, δ): 0.90 (3H, m)
FD Mass: 810 (M$^+$+1)

(6) 3''-N-[(R,S)-2-Hydroxypropionyl]-1-N-palmitoylkanamycin A dihydrochloride.
mp; >122° C. (dec.).
IR (Nujol): 1700, 1630, 1220, 1120, 1070 cm$^{-1}$
NMR (CD$_3$OD, δ): 0.90 (3H, m)

(7) 3''-N-[(D,L)-2,4-diaminobutyryl]-1-N-palmitoylkanamycin A tetrahydrochloride.
mp; >125° C. (dec.).
IR (Film-MeOH): 1710, 1640, 1540, 1215, 1070 cm$^{-1}$
NMR (CD$_3$OD, δ): 0.92 (3H, m)

(8) 1-N-n-Tridecyloxycarbonyl-3''-N-trifluoroacetylkanamycin A dihydrochloride.
mp; >132° C. (dec.).
IR (Nujol): 3300, 1700, 1540, 1270, 1155, 1030 cm$^{-1}$
NMR (CD$_3$OD, δ): 0.95 (3H, m)
FD Mass: 808 (M$^+$+1)

(9) 1-N-n-Tetradecyloxycarbonyl-3''-N-trifluoroacetylkanamycin A dihydrochloride.
mp; >153° C. (dec.).
IR (Nujol): 3280, 1700, 1560, 1270, 1150, 1030 cm$^{-1}$
NMR (CD$_3$OD, δ): 0.95 (3H, m), 5.18 (1H, d, J=3 Hz)

(10) 1-N-n-Pentadecyloxycarbonyl-3''-N-trifluoroacetylkanamycin A dihydrochloride.
mp; >179° C. (dec.).
IR (Nujol): 3280, 1700, 1540, 1260, 1150, 1040 cm$^{-1}$
NMR (CD$_3$OD, δ): 0.95 (3H, m), 5.10 (1H, d, J=3 Hz)

(11) 1-N-n-Heptadecyloxycarbonyl-3''-N-trifluoroacetylkanamycin A dihydrochloride.
mp; >159° C. (dec.).
IR (Nujol): 3300, 1700, 1550, 1270, 1155, 1030 cm$^{-1}$
NMR (CD$_3$OD, δ): 0.95 (3H, m), 5.12 (1H, d, J=4 Hz), 5.48 (1H, d, J=3 Hz)

(12) 1-N-n-Octadecyloxycarbonyl-3''-N-trifluoroacetylkanamycin A dihydrochloride.
mp; >219° C.
IR (Nujol): 3300, 1700, 1540, 1270, 1210, 1160, 1030 cm$^{-1}$
NMR (CD$_3$OD, δ): 0.95 (3H, m) 5.15 (1H, d, J=3 Hz)
FD Mass; 876 (M$^+$−1), 898 (M$^+$+Na)

(13) 1-N-n-Nonadecyloxycarbonyl-3''-N-trifluoroacetylkanamycin A dihydrochloride.
mp; >96° C. (dec.).
IR (Nujol): 3320, 1700, 1270, 1155, 1030 cm$^{-1}$
NMR (CD$_3$OD, δ): 0.96 (3H, m)

(14) 3''-N-Trifluoroacetyl-1-N-(3,7,11-trimethyldodecyloxycarbonyl)kanamycin A dihydrochloride.
mp; >211° C. (dec.).
IR (Nujol): 3280, 1700, 1540, 1270, 1155, 1030 cm$^{-1}$
NMR (CD$_3$OD, δ): 5.12 (1H, d, J=3 Hz), 5.50 (1H, d, J=2 Hz)
FD Mass: 856 (M$^+$+Na)

(15) 1-N-(1-Methyltridecyloxycarbonyl)-3''-N-trifluoroacetylkanamycin A dihydrochloride.
mp; >133° C. (dec.).
IR (Nujol): 3250, 1700, 1270, 1155, 1030 cm$^{-1}$
NMR (CD$_3$OD, δ): 0.95 (3H, m), 5.15 (1H, d, J=3 Hz)

(16) 3''-N-Carbamoyl-1-N-palmitoylkanamycin A dihydrochloride.
mp; >194° C. (dec.).
IR (Nujol): 3250, 1700, 1630, 1540, 1240, 1140, 1030 cm$^{-1}$
NMR (CD$_3$OD, δ): 0.95 (3H, m), 5.10 (1H, d, J=3 Hz), 5.51 (1H, d, J=3 Hz)

(17) 1-N-[(R,S)-3-Dodecanoyloxytetradecanoyl]-3''-N-glycylkanamycin A trihydrochloride.
mp; >147° C. (dec.).
IR (Nujol): 3200, 1680, 1540, 1040, 1030 cm$^{-1}$
NMR (CD$_3$OD, δ): 0.93 (3H, m)

(18) 3''-N-Glycyl-1-N-[(R,S)-3-hydroxyoctadecanoyl]-kanamycin A trihydrochloride.
mp; >193° C. (dec.).
IR (Nujol): 3300, 1640, 1560, 1140, 1030 cm$^{-1}$
NMR (CD$_3$OD, δ): 0.93 (3H, m)

(19) 3''-N-Glycyl-1-N-[(R,S)-3-hydroxydecanoyl]kanamycin A trihydrochloride.
mp; >209° C. (dec.).
IR (Nujol): 3200, 1630, 1560, 1140, 1010 cm$^{-1}$
NMR (CD$_3$OD, δ): 0.96 (3H, m), 5.52 (1H, d, J=3 Hz)

(20) 3''-N-Glycyl-1-N-[(R,S)-3-hydroxy-n-hexadecanoyl]kanamycin A trihydrochloride.
mp; >223° C. (dec.).
IR (Nujol): 3200, 1630, 1550, 1140, 1080, 1025 cm$^{-1}$
NMR (CD$_3$OD, δ): 0.93 (3H, m), 5.50 (1H, d, J=3 Hz)

Example 37

The following compound was obtained according to a similar manner to that of Example 13 (2).
3,6'-Bis-N-benzyloxycarbonyl-1-N-n-pentadecanoylkanamycin A.
IR (Nujol): 1710, 1685, 1640, 1530, 1265, 1140, 1045 cm$^{-1}$.
NMR (DMSO-d$_6$, δ): 0.86 (3H, m)

Example 38

To a solution of 1-N-n-pentadecanoyl-3''-N-trifluoroacetylkanamycin A dihydrochloride (500 mg) in water (20 ml) was added α-cyclodextrin (554 mg) at ambient temperature. The mixture was stirred at the same temperature for an hour. The solution was filtered off and lyophilized to give 1-N-n-pentadecanoyl-3''-N-trifluoroacetylkanamycin A dihydrochloride-α-cyclodextrin complex (1:1 mol/mol) (1.02 g).
mp; >221° C. (dec.).
IR (Nujol): 3300, 1700, 1630, 1150, 1080, 1020 cm$^{-1}$
NMR (CD$_3$OD, δ): 0.95 (3H, m)

Example 39

To a solution of 1-N-palmitoyl-3''-N-trifluoroacetylkanamycin A dihydrochloride (500 mg) in methanol (10 ml) was added urea (438 mg) at ambient temperature. The mixture was stirred at the same temperature for 10 minutes. The solution was concentrated under reduced pressure to give a residue. The residue was dissolved in water (30 ml) and the solution was filtered off and lyophilized to give 1-N-palmitoyl-3''-N-trifluoroacetylkanamycin A dihydrochloride-urea complex (1:13 mol/mol) (907 mg).
mp; >212° C. (dec.).
IR (Nujol): 3420, 3320, 3200, 1680, 1625, 1590, 1150, 1025 cm$^{-1}$
NMR (D$_2$O, δ): 0.90 (3H, m)

Example 40

The following compounds were obtained according to a similar manner to that of Example 38.

(1) 1-N-n-Pentadecanoyl-3''-N-trifluoroacetylkanamycin A dihydrochloride-α-cyclodextrin complex (1:2 mol/mol).
mp; >227° C. (dec.).
IR (Nujol): 3300, 1710, 1635, 1150, 1080, 1030 cm$^{-1}$
NMR (CD$_3$OD, δ): 0.92 (3H, m)

(2) 1-N-Palmitoyl-3''-N-trifluoroacetylkanamycin A dihydrochloride-γ-cyclodextrin complex (1:2 mol/mol)
mp; >224° C. (dec.).
[α]$_D^{20}$; +132.9° (C1.0 H$_2$O)
IR (Nujol): 1710, 1630, 1150, 1070, 1010 cm$^{-1}$
NMR (CD$_3$OD, δ): 0.93 (3H, m)

(3) 1-N-Palmitoyl-3''-N-trifluoroacetylkanamycin A dihydrochloride-β-cyclodextrin complex (1:2 mol/mol).
mp; >210° C. (dec.).
[α]$_D^{20}$; +81.7° (C1.0 H$_2$O)
IR (Nujol): 3300, 1700, 1630, 1150, 1080, 1020 cm$^{-1}$
NMR (CD$_3$OD-D$_2$O, δ): 0.91 (3H, m)

(4) 1-N-Palmitoyl-3''-N-trifluoroacetylkanamycin A dihydrochloride-β-cyclodextrin complex (1:1 mol/mol).
mp; >214° C. (dec.).
[α]$_D^{20}$; +89.7° (C1,0 H$_2$O)
IR (Nujol): 3300, 1705, 1635, 1150, 1080, 1030 cm$^{-1}$
NMR (CD$_3$OD-D$_2$O)δ: 0.90 (3H, m)

(5) 1-N-Palmitoyl-3''-N-trifluoroacetylkanamycin A dihydrochloride-α-cyclodextrin complex (1:2 mol/mol).
mp; >222° C. (dec.).
[α]$_D^{20}$; +82.5° (C1,0 H$_2$O)
IR (Nujol): 3300, 1710, 1630, 1150, 1080, 1030 cm$^{-1}$
NMR (CD$_3$OD, δ): 0.95 (3H, m)

(6) 1-N-Palmitoyl-3''-N-trifluoroacetylkanamycin A dihydrochloride-α-cyclodextrin complex (1:1 mol/mol).
mp; >219° C. (dec.).
[α]$_D^{20}$; +82.6° (C1,0 H$_2$O)
IR (Nujol): 3300, 1710, 1630, 1150, 1080, 1030 cm$^{-1}$
NMR (CD$_3$OD, δ): 0.92 (3H, m)

(7) 1-N-n-Icosanoyl-3''-N-trifluoroacetylkanamycin A dihydrochloride-α-cyclodextrin complex (1:2 mol/mol)
mp; >225° C. (dec.).
[α]$_D^{20}$; +84.24° (C1,0 H$_2$O)
IR (Nujol): 3300, 1700, 1630, 1150, 1080, 1025 cm$^{-1}$ Example 41

The following compounds were obtained according to a similar manner to that of Example 26.
(1) 3,6'-Bis-N-benzyloxycarbonyl-3''-N-benzyloxycarbonylcarbamoyl-1-N-palmitoylkanamycin A.
IR (Nujol): 3300, 1785, 1740, 1685, 1530, 1300, 1250, 1040 cm$^{-1}$
NMR (DMSO-d$_6$, δ): 0.90 (3H, m).
(2) 3,6'-Bis-N-benzyloxycarbonyl-3''-N-[N-(benzyloxycarbonyl)phenyl]-1-N-[(R,S)-3-hydroxyoctadecanoyl]kanamycin A.
IR (Nujol): 3300, 1690, 1640, 1540, 1040 cm$^{-1}$
NMR (DMSO-d$_6$, δ): 0.90 (3H, m)
(3) 3,6'-Bis-N-benzyloxycarbonyl-3''-N-(N-benzyloxycarbonyl)glycyl-1-N-[(R,S)-3-hydroxydecanoyl]kanamycin A.
IR (Nujol): 3300, 1695, 1640, 1540, 1270, 1150, 1040 cm$^{-1}$
NMR (DMSO-d$_6$, δ): 0.91 (3H, m)
(4) 3,6'-Bis-N-benzyloxycarbonyl-3''-N-(N-benzyloxycarbonyl)glycyl-1-N-[(R,S)-3-hydroxyhexadecanoyl]kanamycin A.

IR (Nujol): 3300, 1690, 1640, 1540, 1270, 1155, 1050 cm$^{-1}$
NMR (DMSO-d$_6$, δ): 0.91 (3H, m)

Example 42

The following compounds were obtained according to a similar manner to that of Example 17 (1) and 17 (2).
(1)
(1) 3,6'-Bis-N-benzyloxycarbonyl-2',3',4',2'',4'',6''-hexa-O-acetyl-1-N-[(R,S)-3-acetoxyoctadecanoyl]-3''-N-trifluoroacetylkanamycin A.
IR (Nujol-EtOH): 1740, 1650, 1540, 1230, 1155, 1030 cm$^{-1}$
NMR (CDCl$_3$, δ): 0.93 (3H, m)
(2) 3,6'-Bis-N-benzyloxycarbonyl-1-N-[(R,S)-3-hydroxyoctadecanoyl]kanamycin A.
IR (Nujol): 3300, 1680, 1640, 1540, 1150 cm$^{-1}$
NMR (DMSO-d$_6$, δ): 0.90 (3H, m).

(2)
(1) 2',3',4',2'',4'',6''-Hexa-O-acetyl-1-N-[(R,S)-3-acetoxydecanoyl]-3,6'-bis-N-benzyloxycarbonyl-3''-N-trifluoroacetylkanamycin A.
IR (Nujol): 1750, 1645, 1230, 1155, 1040 cm$^{-1}$
NMR (CDCl$_3$, δ): 0.95 (3H, m)
(2) 3,6'-Bis-N-benzyloxycarbonyl-1-N-[(R,S)-3-hydroxydecanoyl]kanamycin A.
IR (Nujol): 3300, 1690, 1640, 1540, 1150, 1050 cm$^{-1}$
NMR (DMSO-d$_6$, δ): 0.92 (3H, m)

(3)
(1) 2',3',4',2'',4'',6''-Hexa-O-acetyl-1-N-[(R,S)-3-acetoxyhexadecanoyl]-3,6'-bis-N-benzyloxycarbonyl-3''-N-trifluoroacetylkanamycin A.
IR (Nujol): 3320, 1740 (sh), 1700, 1640, 1540, 1260, 1170, 1060 cm$^{-1}$
NMR (CDCl$_3$, δ): 0.95 (3H, m)
(2) 3,6'-Bis-N-benzyloxycarbonyl-1-N-[(R,S)-3-hydroxyhexadecanoyl]kanamycin A.
IR (Nujol): 1690, 1640, 1540, 1270, 1230, 1150 cm$^{-1}$
NMR (DMSO-d$_6$, δ): 0.90 (3H, m).

What we claim is:
1. Aminoglycoside derivatives of the formula:

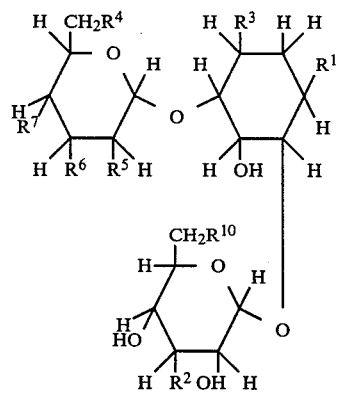

wherein
at least one of R$^1$, R$^2$, R$^3$ and R$^4$ is C$_8$-C$_{24}$ alkanoylamino, C$_8$-C$_{24}$ alkenoylamino, C$_8$-C$_{20}$ alkoxycarbonylamino, C$_8$-C$_{18}$ alkylaminocarbonylamino, C$_8$-C$_{20}$ alkoxy C$_1$-C$_6$alkanoylamino or C$_8$-C$_{18}$ alkylthiocarbonylamino, each of which is unsubstituted or substituted with hydroxy, amino, carboxy, C$_1$-C$_6$ alkyl, C$_1$-C$_6$ alkoxy, C$_1$-C$_6$ alkylthio, halogen, nitro, acylamino, aryloxy, C$_1$-C$_6$ alkanoyloxy, or C$_8$-C$_{24}$ alkanoyloxy, and the others are amino or acylamino, $R^5$ is hydroxy, amino or acylamino,
$R^6$ and $R^7$ are each hydroxy or hydrogen, and
$R^{10}$ is hydroxy or phosphonoxy; or
pharmaceutically acceptable salts thereof.

2. The compound of claim 1, wherein at least one of $R^1$, $R^2$, $R^3$ and $R^4$ is $C_8$–$C_{24}$ alkanoylamino, $C_8$–$C_{24}$ alkenoylamino, $C_8$–$C_{20}$ alkoxycarbonylamino, $C_8$–$C_{18}$ alkylaminocarbonylamino, $C_8$–$C_{20}$ alkoxy $C_1$–$C_6$alkanoylamino or $C_8$–$C_{18}$ alkylthiocarbonylamino, each of which may have lower alkyl, hydroxy, $C_1$–$C_6$ alkanoyloxy or $C_8$–$C_{24}$ alkanoyloxy, and the others are amino, carbamoylamino, aroylamino, $C_1$–$C_6$ alkoxycarbonylamino, or $C_1$–$C_6$ alkanoylamino which may have hydroxy, amino, carboxy or halogen, and $R^5$ is hydroxy, amino or phenyl $C_1$–$C_6$alkoxycarbonylamino.

3. The compound of claim 2, wherein at least one of $R^1$, $R^2$, $R^3$ and $R^4$ is $C_8$–$C_{24}$ alkanoylamino which may have $C_1$–$C_6$ alkyl, hydroxy, $C_1$–$C_6$ alkanoyloxy or $C_8$–$C_{24}$ alkanoyloxy; $C_8$–$C_{24}$ alkenoylamino; $C_8$–$C_{20}$ alkoxycarbonylamino which may have $C_1$–$C_6$ alkyl; $C_8$–$C_{18}$ alkylaminocarbonylamino; $C_8$–$C_{20}$ alkoxy $C_1$–$C_6$alkanoylamino or $C_8$–$C_{18}$ alkylthiocarbonylamino.

4. The compound of claim 3, wherein one of $R^1$, $R^2$, $R^3$ and $R^4$ is octanoylamino, nonanoylamino, decanoylamino, decanoylamino having hexyl or hydroxy, undecanoylamino, lauroylamino, myristoylamino, myristoylamino having hydroxy, myristoylamino having acetyloxy, myristoylamino having lauroyloxy, pentadecanoylamino, palmitoylamino, palmitoylamino having hydroxy, heptadecanoylamino, stearoylamino, stearoylamino having hydroxy, icosanoylamino, dodecyloxycarbonylamino, dodecyloxycarbonylamino having methyl, tridecyloxycarbonylamino, tridecyloxycarbonylamino having methyl, tetradecyloxycarbonylamino, pentadecyloxycarbonylamino, hexadecyloxycarbonylamino, heptadecyloxycarbonylamino, octadecyloxycarbonylamino, nonadecyloxycarbonylamino, pentadecylaminocarbonylamino, tridecyloxyacetylamino or hexadecylthiocarbonylamino, and the others are amino, carbamoylamino, acetylamino, trifluoroacetylamino, octanoylamino, t-butoxycarbonylamino, aminoacetylamino, carboxypropionylamino, hydroxyacetylamino, propionylamino, benzoylamino, propionylamino having hydroxy, butyrylamino having hydroxy, butyrylamino having amino, and $R^5$ is hydroxy, amino or benzyloxycarbonylamino.

5. The compound of claim 4, which is 1-N-n-icosanoyl-3''-N-trifluoroacetylkanamycin A dihydrochloride.

6. The compound of claim 4, which is 1-N-n-hexadecyloxycarbonyl-3''-N-trifluoroacetylkanamycin A dihydrochloride.

7. Aminoglycoside derivatives of the formula:

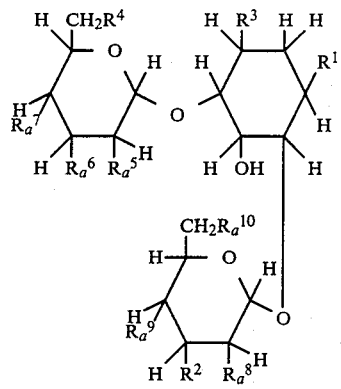

wherein
$R_a^5$, $R_a^6$, $R_a^7$, $R_a^8$, $R_a^9$ and $R_a^{10}$ are each acyloxy, and
$R^1$ is $C_8$–$C_{24}$ alkanoylamino, $C_8$–$C_{24}$ alkenoylamino, $C_8$–$C_{20}$ alkoxycarbonylamino, $C_8$–$C_{18}$ alkylaminocarbonylamino, $C_8$–$C_{20}$ alkoxy $C_1$–$C_6$alkanoylamino or $C_8$–$C_{18}$ alkylthiocarbonylamino, each of which is unsubstituted or substituted with hydroxy, amino, carboxy, $C_1$–$C_6$ alkyl, $C_1$–$C_6$ alkoxy, $C_1$–$C_6$ alkylthio, halogen, nitro, acylamino, aryloxy, or $C_1$–$C_6$ and $C_8$–$C_{24}$ alkanoyloxy, and
$R^2$, $R^3$ and $R^4$ are each amino or acylamino; or
a salt thereof.

8. A pharmaceutical composition comprising an antiviral effective amount of compound of claim 1 or pharmaceutically acceptable salt thereof and a pharmaceutically acceptable, substantially non-toxic carrier or excipient.

9. A method of treating herpes simplex virus comprising administering to a host in need of such treatment an anti-viral effective amount of the aminoglycoside derivative of claim 1.

10. The method of claim 9 wherein the amount of the aminoglycoside derivative is from 0.1 to 100 mg/kg/day.

11. The pharmaceutical composition of claim 8 in unit dosage form.

12. The pharmaceutical composition of claim 8 suitable for oral, parenteral and external administration.

13. The pharmaceutical composition of claim 8 wherein the carrier is an organic or inorganic solid or liquid excipient.

14. The pharmaceutical composition of claim 8 in solid form.

15. The pharmaceutical composition of claim 13 in the form of a tablet, dragee, ointment, granule, powder or capsule.

16. The pharmaceutical composition of claim 8 in liquid form.

17. The pharmaceutical composition of claim 15 in the form of a solution, suspension, syrup, emulsion or lemonade.

18. The pharmaceutical composition of claim 8 further comprising an additive selected from the group consisting of a stabilizing agent, wetting agent, lactose, magnesium stearate, terra alba, sucrose, corn starch, talc, stearic acid, gelatin, agar, pectin, peanut oil, olive oil, cocoa butter, and ethylene glycol.

* * * * *